(12) United States Patent
Suri et al.

(10) Patent No.: US 10,352,941 B2
(45) Date of Patent: Jul. 16, 2019

(54) METHOD FOR FUNCTIONALIZING A POROUS MEMBRANE COVERING OF AN OPTICAL SENSOR TO FACILITATE COUPLING OF AN ANTITHROM-BOGENIC AGENT

(71) Applicant: MEDTRONIC MINIMED, INC., Northridge, CA (US)

(72) Inventors: Jeff T. Suri, Rancho Santa Margarita, CA (US); Eric Patterson, Los Angeles, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 719 days.

(21) Appl. No.: 14/347,567

(22) PCT Filed: Sep. 25, 2012

(86) PCT No.: PCT/US2012/057127
§ 371 (c)(1),
(2) Date: Mar. 26, 2014

(87) PCT Pub. No.: WO2013/049068
PCT Pub. Date: Apr. 4, 2013

(65) Prior Publication Data
US 2014/0242710 A1    Aug. 28, 2014

Related U.S. Application Data

(60) Provisional application No. 61/539,832, filed on Sep. 27, 2011.

(51) Int. Cl.
*G01N 33/66* (2006.01)
*A61L 33/00* (2006.01)
(Continued)

(52) U.S. Cl.
CPC .......... *G01N 33/66* (2013.01); *A61L 33/0023* (2013.01); *G01N 33/54393* (2013.01);
(Continued)

(58) Field of Classification Search
CPC ................ A61L 33/0023; G01N 33/66; G01N 33/54393; G01N 2650/00; G01N 2400/40; Y10T 436/144444; B05D 3/142
(Continued)

(56) References Cited

U.S. PATENT DOCUMENTS 4,755,173 A    7/1988 Konopka et al.
5,391,250 A    2/1995 Cheney, II et al.
(Continued)

OTHER PUBLICATIONS

PCT International Search Report and Written Opinion for PCT/US2012/057127 dated Feb. 15, 2013.
(Continued)

*Primary Examiner* — Rebecca M Fritchman

(57) ABSTRACT

Methods of covalently attaching heparin to a membrane comprising plasma treating the membrane to produce an amino-functionalized membrane; and reacting the amino-functionalized membrane with heparin under conditions in which heparin becomes covalently attached to the amino-functionalized membrane, wherein said heparin is indirectly attached via a spacer to said amino-functionalized membrane and/or said heparin is attached from a single site in said heparin to a single site on said amino-functionalized membrane or to said spacer. Also disclosed are analyte sensors.

19 Claims, 10 Drawing Sheets

(51) Int. Cl.
*G01N 33/543* (2006.01)
*G01N 33/00* (2006.01)
*B05D 3/14* (2006.01)

(52) U.S. Cl.
CPC .......... *B05D 3/142* (2013.01); *G01N 2400/40* (2013.01); *G01N 2650/00* (2013.01); *Y10T 436/144444* (2015.01)

(58) Field of Classification Search
USPC .......................................................... 436/95
See application file for complete search history.

(56) References Cited

U.S. PATENT DOCUMENTS

| | | | |
|---|---|---|---|
| 5,485,408 A | 1/1996 | Blomquist | |
| 5,522,803 A | 6/1996 | Teissen-Simony | |
| 5,643,580 A * | 7/1997 | Subramaniam | A61L 33/0011 424/400 |
| 5,650,234 A * | 7/1997 | Dolence | C07D 207/46 427/2.3 |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2005/0266038 A1 * | 12/2005 | Glauser | A61L 31/10 424/423 |
| 2006/0039950 A1 * | 2/2006 | Zhou | A61K 31/655 424/423 |
| 2007/0123819 A1 | 5/2007 | Mernoe et al. | |
| 2009/0112075 A1 * | 4/2009 | Klok | A61B 5/0031 600/365 |
| 2009/0200620 A1 * | 8/2009 | Omura | B81B 3/0021 257/419 |
| 2010/0160861 A1 | 6/2010 | Causey, III et al. | |
| 2011/0077477 A1 * | 3/2011 | Romey | A61B 5/14532 600/309 |
| 2012/0028275 A1 * | 2/2012 | Kieferle | C12M 25/10 435/7.21 |

OTHER PUBLICATIONS

Baihai Su, Shudong Sun and Changsheng Zhao, Nov. 7, 2011 (Nov. 7, 2011). Polyethersulfone Hollow Fiber Membranes for Hemodialysis, Progress in Hemodialysis—From Emergent Biotechnology to Clinical Practice, Prof. Angelo Carpi (Ed.), ISBN: 978-953-307-377-4, In Tech, Available from: http://www.intechopen.com/books/progress-inhemodialysisfrom-emergent-biotechnology-to-clinical-practice/polyethersulfone-hollow-fiber-membranes-forhemodialysis.

* cited by examiner

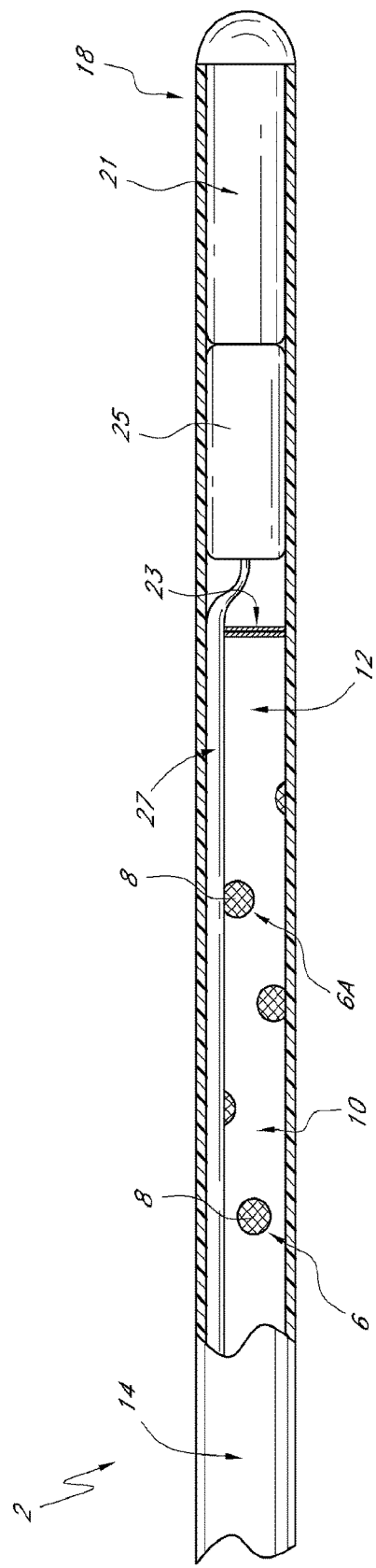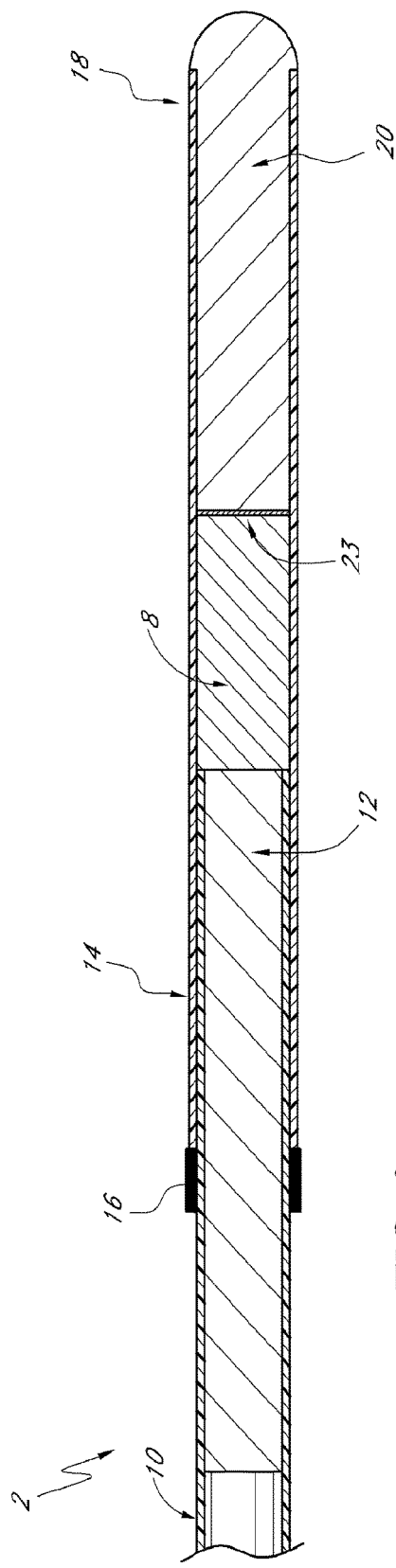
FIG. 1
FIG. 2

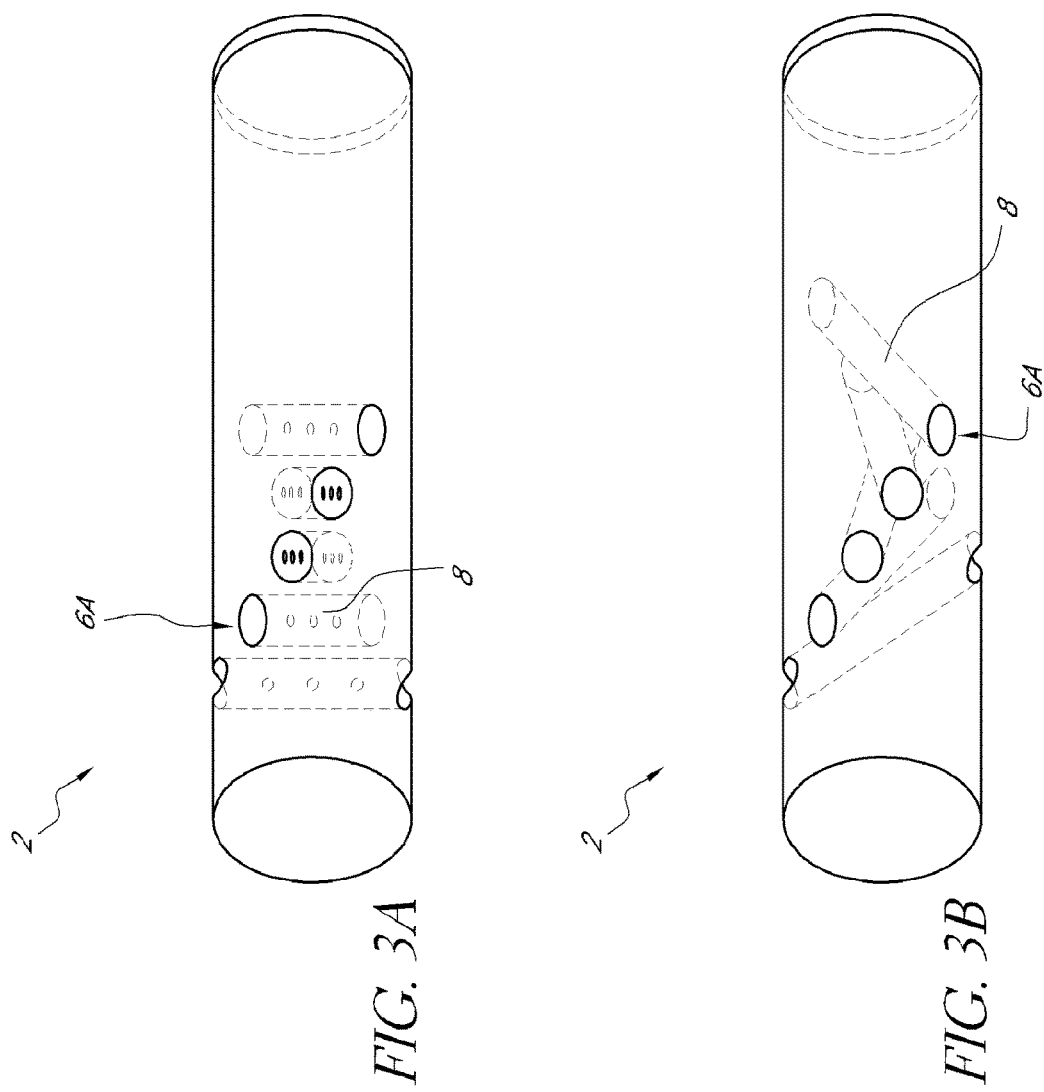

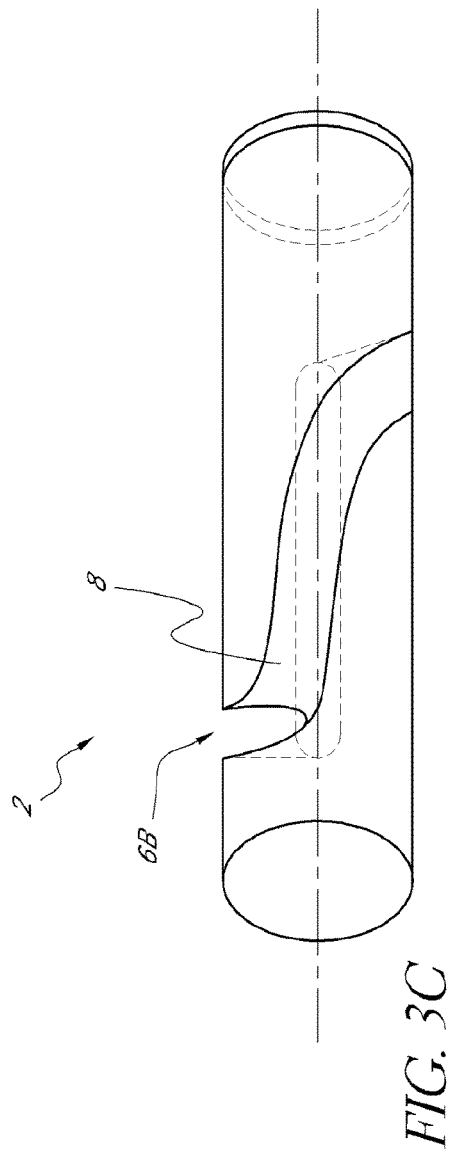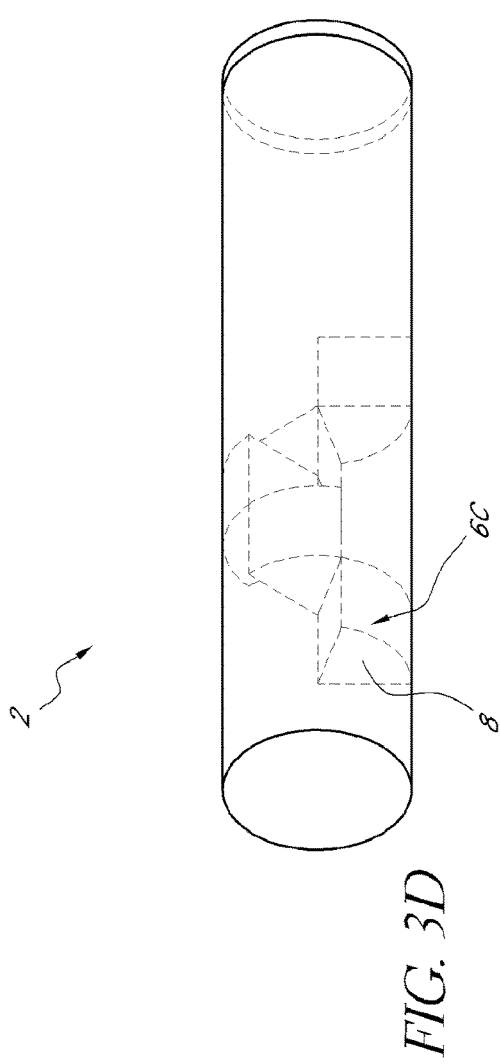
FIG. 3C
FIG. 3D

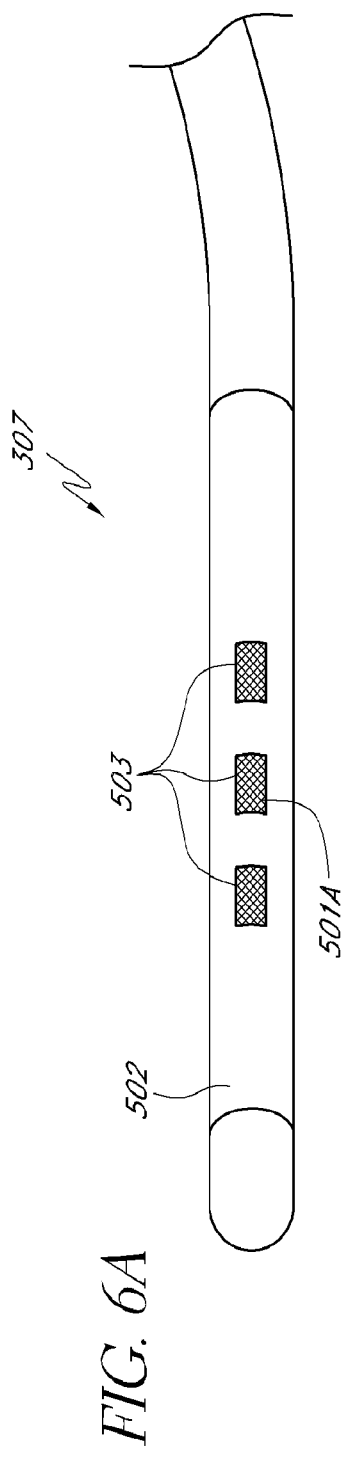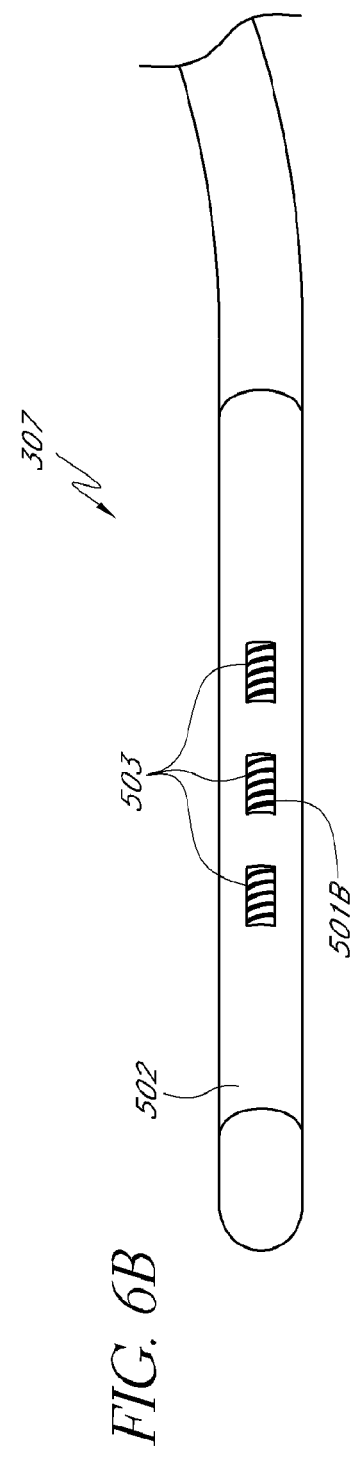

Non-Porous Precursor Section

Microporous Membrane Section

METHOD FOR FUNCTIONALIZING A POROUS MEMBRANE COVERING OF AN OPTICAL SENSOR TO FACILITATE COUPLING OF AN ANTITHROM-BOGENIC AGENT

BACKGROUND OF THE INVENTION

Field of the Invention

Embodiments of the present invention generally relate to thromboresistant coatings for medical devices, such as intravascular glucose sensors, having a blood-contacting surface, as well as to methods for forming such coatings, and to the medical devices thus formed.

Description of the Related Art

Achieving glycemic control is facilitated by continuous or nearly continuous monitoring of patient blood glucose levels. One method for accomplishing such monitoring is through the use of an implanted glucose sensor. For example, an optical glucose sensor, such as those disclosed in U.S. Pat. Nos. 5,137,033, 5,512,246, 5,503,770, 6,627,177, 7,417,164 and 7,470,420, and U.S. Patent Publ. Nos. 2006/0083688, 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 61/045,887 (each of which is incorporated herein in its entirety by reference thereto), can be deployed in the vascular system of the patient, with glucose readings taken continuously, or as needed. Of course, any indwelling intravascular glucose sensor can potentially be used in monitoring glucose for the purpose of achieving glycemic control.

The presence of foreign bodies in the vascular system of patients, such as intravascular glucose sensors, can lead to the formation of a blood clot or thrombus around the sensor. In some cases, the thrombus can result in the restriction of blood flow through the blood vessel, impairing functionality of the sensor and/or health of the patient. In some cases, the thrombus can break off and travel through the bloodstream to other parts of the body, such as the heart or brain, leading to severe health problems. As result, it is desirable to minimize the formation of a thrombus on or near the sensor.

Heparin has been used clinically for decades as an intravenous anticoagulant to treat clotting disorders and to prevent thrombus formation during surgery and interventional procedures. Coating the outer surface of a medical device, e.g., stents, prostheses, catheters, tubing, and blood storage vessels, with heparin or a heparin containing complex (See, e.g., U.S. Reissued Pat. No. RE39,438 to Shah, et al.) may reduce the thrombogenecity of the device when it comes into contact with blood by: (1) inhibiting enzymes critical to the formation of fibrin (which holds thrombi together); (2) reducing the adsorption of blood proteins, which may lead to undesirable reactions on the device surface; and (3) reducing the adhesion and activation of platelets, which play an important role in thrombogenesis. Ideally, the heparin coating substantially shields the blood from the underlying surface of the medical device, such that the blood components contact the heparin coating rather than the device surface, thus reducing the formation of thrombi or emboli (blood clots that release and travel downstream).

Unfortunately, depending on the surface material of the device, heparin may not provide a lasting and/or contiguous thromboresistant coating. Various strategies have been implemented to enhance the integrity of the heparin coating. For example, photo-activated coupling methods can be used to covalently bind heparin to a device surface thereby extending the useful life of the coating (See e.g., Surmodics' PHOTOLINK® process at www.surmodics.com/technologies-surface-biocompatibility-heparin.html). Alternatively, for certain materials, e.g., PVC, linkers such as tridodecylmethyl ammonium chloride (TDMAC) and PEO-polyethylene oxide, among others, have been used to space the heparin molecule away from the PVC surfaces (See e.g., U.S. Pat. No. 5,441,759 to Crouther et al.). Heparin may be cross-linked to polypeptides to create a thromboresistant hydrogel with peptide-specific functionality (See e.g., U.S. Pat. No. 7,303,814 to Lamberti, et al. disclosing a wound-healing functionality). Heparin derivatives or complexes, such as heparin benzalkonium chloride (hereinafter "HBAC"), have also been applied as a thromboresistant coating for medical devices. However, HBAC has not been used with success for devices, such as intravascular analyte sensors, that require passage of the analyte in the blood through the coating. Moreover, Hsu (U.S. Pat. No. 5,047,020) disclosed use of various heparin complexes for coating blood gas sensors and noted that the benzalkonium heparin complex was unsuitable for such an intravascular sensor.

Accordingly, there is an important unmet need for a thromboresistant coating and methods for applying such a coating to an intravascular analyte sensor, and in particular, a glucose sensor.

Covalent heparin modification of polysulfone membranes has been reported for use in ex vivo hemodialysis (Li et al. 2011 *Macromolec Biosci* 11: 1218-1226). The process utilized atmospheric glow discharge, with ammonia and argon gas for plasma treatment of flat sheet, polysulfone (PSF) membranes, which were subsequently modified via 1-Ethyl-3-(dimethylaminopropyl) carbodiimide hydrochloride/N-Hydroxysuccinimide (EDC/NHS) binding chemistry. Others have covalently bound heparin to a polysulfone membrane surface by chloromethylating aromatic rings on the membrane and then reacting with ethylene diamine (EDA) to attach amine groups to the surface (Huang et al. 2011 *Macromolec Biosci* 11: 131-140).

SUMMARY OF THE INVENTION

Embodiments of the invention relate to an analyte sensor, comprising: an elongate member; an analyte-responsive indicator disposed along a distal portion of the elongate member, wherein the indicator is capable of generating a signal related to a concentration of analyte in the blood vessel; a semipermeable membrane covering at least the indicator along the distal portion of the elongate member; and a coating comprising heparin and benzalkonium stably associated with at least a portion of the semipermeable membrane.

In preferred embodiments of the analyte sensor, the elongate member comprises an optical fiber comprising a light path. The analyte-responsive indicator preferably comprises a fluorophore operably coupled to an analyte binding moiety, wherein analyte binding causes a change in the emission intensity of the fluorophore, and wherein the analyte responsive indictor is disposed within the light path of the optical fiber. More preferably, the fluorophore is HPTS-triCysMA and the binding moiety is 3,3'-oBBV.

In certain embodiments, the semipermeable membrane is a porous membrane. The porous membrane may comprise one or more polymers selected from a group consisting of the polyolefins, the fluoropolymers, the polycarbonates, and the polysulfones. More preferably, the porous membrane comprises at least one polysulfone. The at least one polysulfone may be selected from the group consisting of polyethersulfone.

In other embodiments of the analyte sensor, the porous membrane comprises at least one polyolefin. The polyolefin is preferably polyethylene.

In some embodiments of the analyte sensor, the semipermeable membrane does not include polysulfone (PSF).

In some embodiments of the analyte sensor, the semipermeable membrane comprises polyethersulfone/polyvinylpyrrolidone (PES/PVP).

Some embodiments relate to an analyte sensor comprising: an elongate member; an analyte-responsive indicator disposed along a distal portion of the elongate member, wherein said indicator is capable of generating a signal related to a concentration of analyte in a blood vessel; a semipermeable membrane covering at least the indicator along the distal portion of the elongate member; and a coating comprising heparin covalently bound to at least a portion of the semipermeable membrane, wherein said heparin is indirectly attached via a spacer to an amino-functionalized membrane and/or wherein said heparin is attached from a single site in said heparin to a single site on said amino-functionalized membrane or to said spacer.

In some embodiments, the spacer is polyethylene glycol.

In some embodiments, the semipermeable membrane is a porous membrane.

In some embodiments, the semipermeable membrane is associated with a hollow fiber that encloses an analyte responsive indicator.

In some embodiments, a cross-sectional geometry of at least a portion of the sensor is tapered so as to produce generally desirable blood flow characteristics when the sensor is placed in a blood vessel lumen.

An equilibrium intravascular analyte sensor is disclosed in accordance with other embodiments of the invention. The equilibrium intravascular analyte sensor comprises: an optical fiber configured for positioning within a blood vessel and comprising a light path and an outer surface; a chemical indicator system comprising a fluorophore operably coupled to an analyte binding moiety, wherein the fluorophore and analyte binding moiety are immobilized within a water-insoluble organic polymer, and wherein the chemical indicator system is disposed within the light path along a distal portion of the optical fiber; and an antithrombogenic, analyte-permeable coating on at least a portion of the outer surface of the optical fiber and overlying the chemical indicator system disposed therein, wherein the coating comprises heparin covalently cross-linked to the outer surface.

The fluorophore is preferably HPTS-triCysMA and the binding moiety is preferably 3,3'-oBBV.

The equilibrium intravascular analyte sensor may further comprise a porous, analyte-permeable membrane disposed between the chemical indicator system and the antithrombogenic coating.

A method for reducing the thrombogenicity of an analyte sensor is disclosed in accordance with other embodiments of the invention. The method comprises: providing the analyte sensor comprising an elongate optical fiber defining a light path, an equilibrium fluorescent chemical indicator system disposed along a distal region of the optical fiber within the light path, and an analyte-permeable porous membrane, which forms an outer layer of at least a portion of the distal region, wherein the indicator system is covered by the porous membrane; contacting the analyte sensor with a single solution comprising a mixture of heparin and benzalkonium, or with separate first and second solutions, wherein the first solution comprises heparin and the second solution comprises benzalkonium; drying the analyte sensor; and repeating the contacting and drying steps between 2 and 10 times.

In preferred embodiments of the method, the equilibrium fluorescent chemical indicator system comprises a fluorophore and an analyte binding moiety, immobilized within a water-insoluble organic polymer. The fluorophore may be HPTS-triCysMA, the binding moiety may be 3,3'-oBBV, and the water-insoluble organic polymer may be a DMAA (N,N-dimethylacrylamide) hydrogel matrix.

In another embodiment of the invention, a method is disclosed for reducing the thrombogenicity of an analyte sensor. The method comprises: providing the analyte sensor comprising an elongate optical fiber defining a light path, an equilibrium fluorescent chemical indicator system disposed along a distal region of the optical fiber within the light path, and an analyte-permeable porous membrane, which forms an outer surface over at least a portion of the distal region, wherein the indicator system is covered by the porous membrane; providing a photoactivatable chemical linking agent and an antithrombogenic molecule, wherein the linking agent is capable, upon activation, of covalent attachment to the outer surface and the antithrombogenic molecule, wherein the linking agent comprises a charged, nonpolymeric di- or higher functional photoactivatable compound comprising two or more photoreactive groups and one or more charged groups; and activating the two or more photoreactive groups, thereby cross-linking the antithrombogenic molecule to the outer surface.

The equilibrium fluorescent chemical indicator system preferably comprises a fluorophore and an analyte binding moiety, immobilized within a water-insoluble organic polymer. In certain preferred embodiments of the method, the fluorophore is HPTS-triCysMA, the binding moiety is 3,3'-oBBV, and the water-insoluble organic polymer is a DMAA (N,N-dimethylacrylamide) hydrogel matrix.

In certain preferred embodiments of the method, the porous membrane comprises microporous polyethylene.

Some embodiments relate to a method of covalently attaching heparin to a membrane comprising: plasma treating the membrane to produce an amino-functionalized membrane; and reacting the amino-functionalized membrane with heparin under conditions in which heparin becomes covalently attached to the amino-functionalized membrane.

In some embodiments, the heparin is directly attached or indirectly attached via a spacer to said amino-functionalized membrane.

In some embodiments, the heparin is attached from a single site in the heparin to a single site on the amino-functionalized membrane or the spacer.

In some embodiments, the plasma treatment is conducted with radio frequency glow discharge plasma.

In some embodiment, the plasma is selected from the group consisting of $O_2$, allylamine and $NH_3$.

In some embodiments, the spacer is polyethylene glycol (PEG).

In some embodiments, the method of covalently attaching heparin to a membrane comprises the following step:

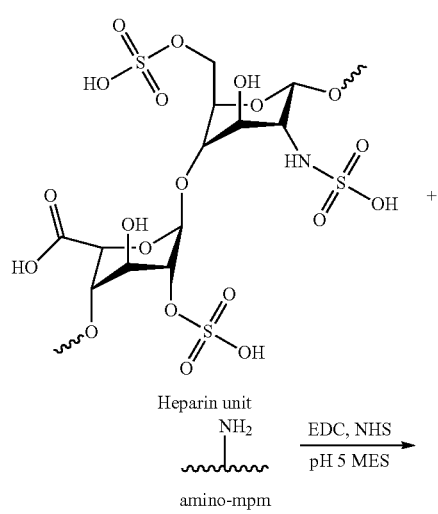
Heparin unit
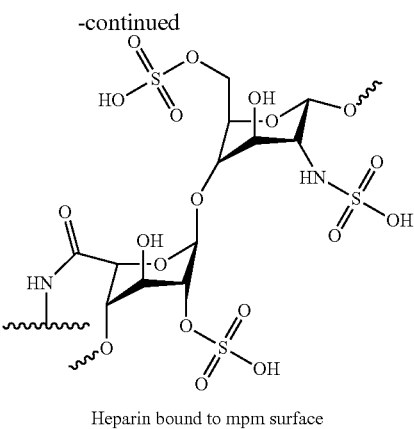
Heparin bound to mpm surface
In some embodiments, the method of covalently attaching heparin to a membrane comprises the following steps:
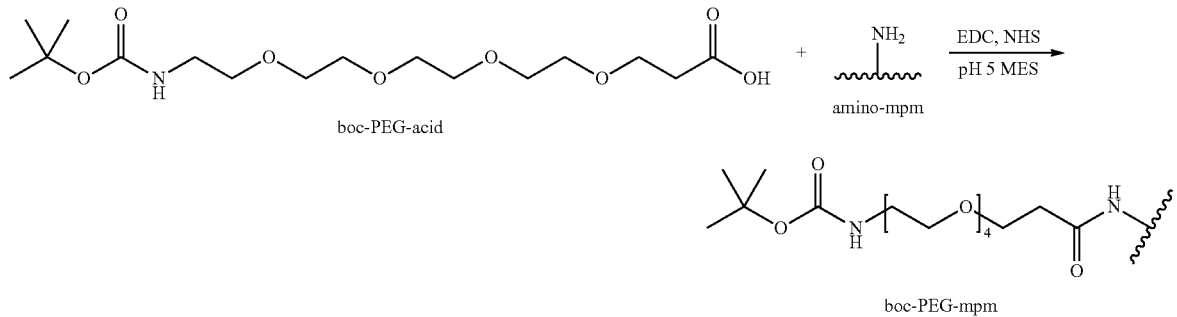
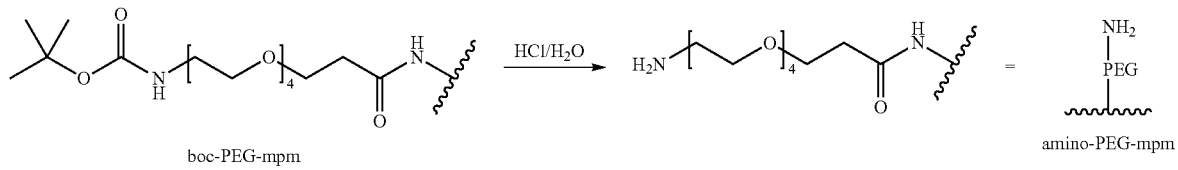
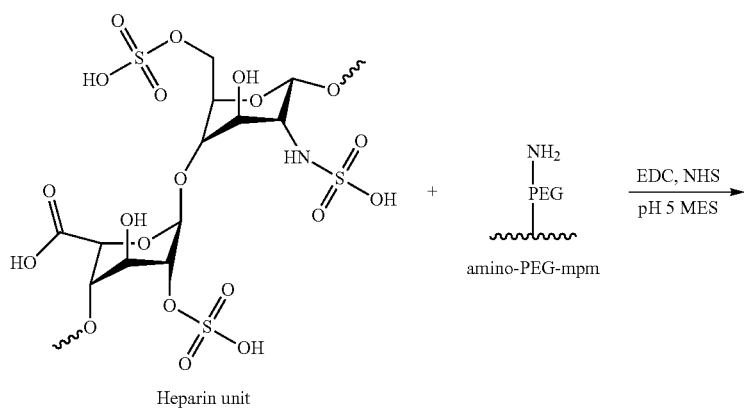

-continued

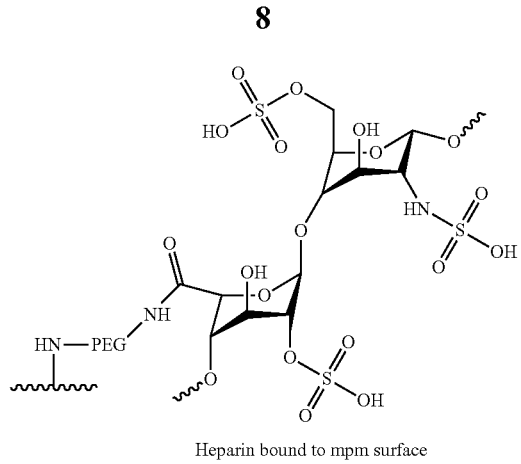

Heparin bound to mpm surface

In some embodiments, the EDC/NHS concentration is 10 mM.

In some embodiments, the membrane is selected from the group consisting of polyethersulfone (PES) membrane, polyethersulfone/polyvinylpyrrolidone (PES/PVP) blend membrane and High Density Polyethylene (HDPE) membrane.

In some embodiments, the membrane is PES membrane.

In some embodiments, the membrane is associated with a hollow fiber that encloses an analyte-responsive indicator.

BRIEF DESCRIPTION OF THE DRAWINGS

FIG. 1 is a cut-away view of a sensor where a portion of the porous membrane sheath is cut away to expose the optical fiber and hydrogel beneath the membrane.

FIG. 2 is a cross-sectional view along a longitudinal axis of a sensor with a hydrogel disposed distal the optical fiber.

FIG. 3A shows a glucose sensor having a series of holes that form a helical configuration.

FIG. 3B shows a glucose sensor having a series of holes drilled or formed at an angle.

FIG. 3C shows a glucose sensor having at least one spiral groove.

FIG. 3D shows a glucose sensor having a series of triangular wedge cut-outs.

FIGS. 6A and 6B show alternative embodiments of an optical glucose sensor, wherein the optical sensor is surrounded by a tubular mesh (FIG. 6A) or coil (FIG. 6B), which is further surrounded by a polymeric material with an open window.

DETAILED DESCRIPTION OF THE PREFERRED EMBODIMENT

Figure 4:
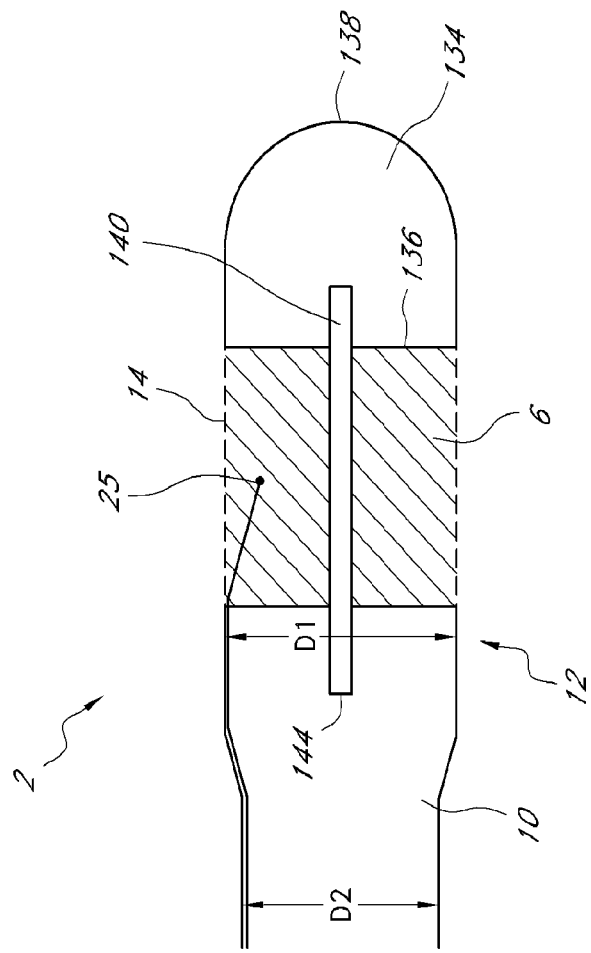
FIG. 4 shows a cross-sectional view of one embodiment of a glucose sensor having a cavity in the distal portion of the sensor.

The following description and examples illustrate a preferred embodiment of the present invention in detail. Those of skill in the art will recognize that there are numerous variations and modifications of this invention that are encompassed within its scope. Accordingly, the description of a preferred embodiment should not be deemed to limit the scope of the present invention.

Various embodiments disclosed herein are generally directed towards analyte sensors configured for in vivo deployment (e.g., intravascular, interstitial, etc.), preferably glucose sensors, wherein the sensors further comprise a thromboresistant outer surface, preferably a coating. Methods of coating sensors to create a thromboresistant outer surface are also disclosed. Of course, intravascular sensors for detecting other analytes besides glucose may also benefit from aspects of the invention, e.g., reducing, inhibiting, and/or preventing blood clot or thrombus formation around the sensor.

Definitions

Unless defined otherwise, technical and scientific terms used herein have the same meaning as commonly understood by one of ordinary skill in the art to which this invention belongs. For purposes of the present invention, the following terms are defined below.

"Porous" is used herein to refer to material that has pores in it to allow permeation of chemical species through the material. The material can be "nanoporous" meaning the material has a mean pore diameter of less than about 2 nm. The material can be "microporous" meaning the material has a mean pore diameter between about 2 nm and about 50 nm. The material can be "mesoporous" meaning that the material has a mean pore diameter of greater than about 50 nm. The material can also be semipermeable, allowing only some chemical species to pass through while preventing or inhibiting other materials from passing through.

"Polyolefin" is used herein to refer to polymers produced from olefins, including copolymers. Two primary examples are polyethylene and polypropylene. Many different grades of these are available, with the grades frequently described in terms of molecular weight or density. Polymers from longer chain monomers than two or three carbons are also included.

"Fluoropolymer" is used herein to refer to polymers that contain chlorine and/or fluorine atoms. Examples include polytetrafluoroethylene, perfluoroalkoxy polymer, fluorinated ethylene-propylene, polyethylenetetrafluoroethylene, polyvinylfluoride, polyethylenechlorotrifluoroethylene, polyvinylidene fluoride, polychlorotrifluoroethylene, perfluoropolyether, perfluoroelastomer, and fluoroelastomer. These materials may be rigid or elastomeric. Trade names include TEFLON, TEFZEL, FLUON, TEDLAR, HALAR, KYNAR, KEL-F, CTFE, KALREZ, TECNOFLON, FFKM, VITON, FOMBLIN, and GALDEN.

"Polycarbonate" is used herein to refer to polymers having functional groups linked by carbonate groups. Trade names include LEXAN, CALIBRE, MAKROLON, PANLITE, and MAKROLIFE.

"Polysulfone" is used herein to refer to polymers containing the sulfone or sulfonyl group, and are most commonly made up of the subunit (aryl 1)-$SO_2$-(aryl 2).

"Heparin" as used herein includes polysaccharide materials having anticoagulant and/or antithrombotic properties, and is frequently referred to as containing alternating derivatives of D-glycocyamine (N-sulfated or N-acetylated) and uranic acid (L-iduronic acid with varying sulfate or D-glucuronic acid) joined by glycosidic linkages, or as including heterogeneous mixtures of variably sulfated polysaccharide chains composed of repeating units of D-glucosamine and either L-iduronic or D-glucuronic acids. Heparin can be derived from natural sources, such as bovine or porcine mucosal tissue, such as from the lung or intestine, and can have varying molecular weight.

"Benzalkonium chloride" is used herein to refer to halogen salts of quaternary ammonium compounds and mixtures of quaternary ammonium compounds primarily having a benzyl and three R-groups attached to the nitrogen, as depicted in the following structure:

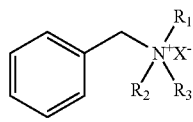

where R1 is in alkyl group having from about one to about five carbons, R2 is an alkyl group having about one to about five carbons, R3 is an alkyl group having about six to about 22 carbons, and $X^-$ is a halogen counterion. While the use of the word "chloride" refers to a specific halogen counter ion having atomic number 17, any halogen counter ion, such as fluoride, chloride, bromide, iodide, etc., with the most commonly used counter ion being chloride may be used in aspects of the present invention. Furthermore, "benzalkonium" is used herein to refer to the quaternary ammonium compound itself. Thus, the halogen salt "benzalkonium chloride" comprises "benzalkonium" and a chloride counter ion. "HBAC" is used herein to refer to complexes of heparin and benzalkonium chloride. Varying grades and molecular weights of heparin can be used. Varying grades of benzalkonium chloride, as well as other salts of benzalkonium ion having various chain lengths for the R-groups, whether in purified or mixed forms, or combined with other related or unrelated compounds can also be used.

GLUCATH® is the proprietary name for an optical glucose sensor configured for intravascular or subcutaneous deployment. In some embodiments, the GLUCATH® sensor has an equilibrium fluorescent chemical indicator system preferably comprising a fluorophore and an analyte binding moiety, immobilized within a water-insoluble organic polymer. In certain embodiments, the fluorophore is HPTS-triCysMA, the binding moiety is 3,3'-oBBV, and the water-insoluble organic polymer is a DMAA (N,N-dimethylacrylamide) hydrogel matrix.

In some embodiments, the equilibrium optical glucose sensor may utilize fluorescent lifetime chemistry as described in US 2009/0018418A1, herein incorporated by reference in its entirety.

Analyte Sensors

Analyte sensors suitable for coating with a thromboresistant surface include those analyte sensors having a polymeric external surface on at least a portion of the sensor. Preferably, that portion of the sensor is configured for in vivo deployment, and more preferably for intravascular deployment. Polymeric materials that can be utilized as a portion of the external surface include hydrophobic polymers such as polyolefins (for example polyethylene and polypropylene), polycarbonate, polysulfone, and fluorocarbons. In some embodiments, the polymeric material can be nanoporous. In some embodiments, the polymeric material can be microporous. In certain such embodiments, the mean pore diameter may be between about 2 nm and about 10 nm, or between about 10 nm and about 20 nm, or between about 20 nm and 30 nm, or between about 30 nm and about 40 nm, or between about 40 nm and about 50 nm, including combinations of the aforementioned ranges. Thus, for example, in certain embodiments, the mean pore diameter may be between about 10 nm and about 30 nm, or between about 20 nm and about 40 nm. In other embodiments, the polymeric material can be mesoporous.

In some embodiments, the porous polymeric surface can be a covering or sheath for at least a portion of the body of the sensor. When the polymeric surface is a covering or sheath, it can be made and/or applied by any suitable method. Sensors can be constructed in various ways, appropriate to the sensing chemistry/technique that is utilized by the sensor. In one embodiment, an optical sensor, such as a sensor producing a fluorescent response in relation to the analyte concentration can have a porous polymeric outer surface for at least a portion of the sensor assembly.

In some embodiments, a sensor can include an insoluble polymeric matrix, which immobilizes the analyte sensitive chemical indicator systems and is sufficiently permeable to the analyte of interest. Suitable polymeric matrix materials include those related to acrylic polymers. In some embodiments, fluorophores and/or binders/quenchers can be incorporated into the polymeric matrix (See e.g., U.S. Pat. Nos. 6,627,177, 7,470,420 and 7,417,164; each of which is incorporated herein in its entirety by reference).

Some embodiments relate to an analyte sensor comprising: an elongate member; an analyte-responsive indicator disposed along a distal portion of the elongate member, wherein said indicator is capable of generating a signal related to a concentration of analyte in a blood vessel; a semipermeable membrane covering at least the indicator along the distal portion of the elongate member; and a coating comprising heparin covalently bound to at least a portion of the semipermeable membrane, wherein said heparin is indirectly attached via a spacer to an amino-functionalized membrane and/or wherein said heparin is attached from a single site in said heparin to a single site on said amino-functionalized membrane or to said spacer.

Any other intravascular glucose sensor may be used in accordance with embodiments of the invention, including for example the electrochemical sensors disclosed in U.S.

Publication Nos. 2008/0119704, 2008/0197024, 2008/0200788, 2008/0200789 and 2008/0200791.

Preferred embodiments of the glucose sensor are configured for implantation into a patient. For example, implantation of the sensor may be made in the arterial or venous systems for direct testing of glucose levels in blood. The site of implantation may affect the particular shape, components, and configuration of the sensor. In some embodiments, the sensor may be configured for interstitial deployment.

Examples of glucose-sensing chemical indicator systems and glucose sensor configurations for intravascular glucose monitoring include the optical sensors disclosed in U.S. Pat. Nos. 5,137,033, 5,512,246, 5,503,770, 6,627,177, 7,417,164 and 7,470,420, and U.S. Patent Publ. Nos. 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 12/424,902; each of which is incorporated herein in its entirety by reference thereto.

Other glucose sensors configured for intravascular deployment include electrochemical sensors, such as those disclosed in U.S. Patent Publ. Nos. 2008/0119704, 2008/0197024, 2008/0200788, 2008/0200789 and 2008/0200791; each of which is incorporated herein in its entirety by reference thereto.

An optical glucose sensor in accordance with preferred embodiments of the present invention comprises a chemical indicator system. Some useful indicator systems comprise a fluorophore operably coupled to an analyte binding moiety, wherein analyte binding causes an apparent optical change in the fluorophore concentration (e.g., emission intensity). For example, a glucose binding moiety such as 3,3'-oBBV that is operably coupled to a fluorescent dye such as HPTS-triCysMA will quench the emission intensity of the fluorescent dye, wherein the extent of quenching is reduced upon glucose binding resulting in an increase in emission intensity related to glucose concentration. In further preferred embodiments, the indicator systems also comprise a means for immobilizing the sensing moieties (e.g., dye-quencher) such that they remain physically close enough to one another to react (quenching). Such immobilizing means are preferably insoluble in an aqueous environment (e.g., intravascular), permeable to the target analytes, and impermeable to the sensing moieties. Typically, the immobilizing means comprises a water-insoluble organic polymer matrix. For example, the HPTS-triCysMA dye and 3,3'-oBBV quencher may be effectively immobilized within a DMAA (N,N-dimethylacrylamide) hydrogel matrix.

Some preferred fluorophores (e.g., HPTS-triCysMA), quenchers/analyte binding moieties (e.g., 3,3'-oBBV) and immobilizing means (e.g., N,N-dimethylacrylamide), as well as methods for synthesizing and assembling such indicator systems are set forth in greater detail in U.S. Pat. Nos. 6,627,177, 7,417,164 and 7,470,420, and U.S. Patent Publ. Nos. 2008/0188722, 2008/0188725, 2008/0187655, 2008/0305009, 2009/0018426, 2009/0018418, and co-pending U.S. patent application Ser. Nos. 12/187,248, 12/172,059, 12/274,617 and 12/424,902.

Other indicator chemistries, such as those disclosed in U.S. Pat. No. 5,176,882 to Gray et al. and U.S. Pat. No. 5,137,833 to Russell, can also be used in accordance with embodiments of the present invention; both of which are incorporated herein in their entireties by reference thereto. In some embodiments, an indicator system may comprise an analyte binding protein operably coupled to a fluorophore, such as the indicator systems and glucose binding proteins disclosed in U.S. Pat. Nos. 6,197,534, 6,227,627, 6,521,447, 6,855,556, 7,064,103, 7,316,909, 7,326,538, 7,345,160, and 7,496,392, U.S. Patent Application Publication Nos. 2003/0232383, 2005/0059097, 2005/0282225, 2009/0104714, 2008/0311675, 2008/0261255, 2007/0136825, 2007/0207498, and 2009/0048430, and PCT International Publication Nos. WO 2009/021052, WO 2009/036070, WO 2009/021026, WO 2009/021039, WO 2003/060464, and WO 2008/072338 which are hereby incorporated by reference herein in their entireties.

FIG. 1 shows a sensor 2 in accordance with an embodiment of the present invention. The sensor comprises an optical fiber 10 with a distal end 12 disposed in a porous membrane sheath 14. The optical fiber 10 has cavities, such as holes 6A, in the fiber optic wall that can be formed by, for example, mechanical means such as drilling or cutting. The holes 6A in the optical fiber 10 can be filled with a suitable compound, such as a polymer. In some embodiments, the polymer is a hydrogel 8. In other embodiments of the sensor 2 as shown in FIG. 2, the optical fiber 10 does not have holes 6A, and instead, the hydrogel 8 is disposed in a space distal to the distal end 12 of the optical fiber 10 and proximal to the mirror 23. In some embodiments, the sensor 2 is a glucose sensor. In some embodiments, the glucose sensor is an intravascular glucose sensor.

In some embodiments, the porous membrane sheath 14 can be made from a polymeric material such as polyethylene, polycarbonate, polyethersulfone, polysulfone, a blend of polyethersulfone/polyvinylpyrrolidone, a high density polyethylene or polypropylene. In some embodiments the porous membrane sheath 14 is a hollow fiber membrane or associated with a hollow fiber membrane. In some embodiments, the porous membrane sheath 14 is not made from polysulfone. Other materials can also be used to make the porous membrane sheath 14 such as zeolites, ceramics, metals, or combinations of these materials. In some embodiments, the porous membrane sheath 14 may be nanoporous. In other embodiments, the porous membrane sheath 14 may be microporous. In still other embodiments, the porous membrane sheath 14 may be mesoporous.

In some embodiments as shown in FIG. 2, the porous membrane sheath 14 is attached to the optical fiber 10 by a connector 16. For example, the connector 16 can be an elastic collar that holds the porous membrane sheath 14 in place by exerting a compressive force on the optical fiber 10, as shown in FIG. 2. In other embodiments, the connector 16 is an adhesive or a thermal weld.

In some embodiments as shown in FIG. 1, a mirror 23 and thermistor 25 can be placed within the porous membrane sheath 14 distal the distal end 12 of the optical fiber 10. Thermistor leads 27 can be made to run in a space between the optical fiber 10 and porous membrane sheath 14. Although a thermistor 25 is shown, other devices such as a thermocouple, pressure transducer, an oxygen sensor, a carbon dioxide sensor or a pH sensor for example can be used instead.

In some embodiments as shown in FIG. 2, the distal end 18 of the porous membrane sheath 14 is open and can be sealed with, for example, an adhesive 20. In some embodiments, the adhesive 20 can comprise a polymerizable material that can fill the distal end 18 and then be polymerized into a plug. Alternatively, in other embodiments the distal end 18 can be thermally welded by melting a portion of the polymeric material on the distal end 18, closing the opening and allowing the melted polymeric material to resolidify. In other embodiments as shown in FIG. 1, a polymeric plug 21 can be inserted into the distal end 18 and thermally heated to weld the plug to the porous membrane sheath 14. Themoplastic polymeric materials such as polyethylene, polypropylene, polycarbonate and polysulfone are particularly suited for thermal welding. In other embodiments, the distal end 18 of the porous membrane sheath 14 can be sealed against the optical fiber 10.

After the porous membrane sheath 14 is attached to the optical fiber 10 and the distal end 18 of the porous membrane sheath 14 is sealed, the sensor 2 can be vacuum filled with a first solution comprising a monomer, a crosslinker and a first initiator. Vacuum filling of a polymerizable solution through a porous membrane and into a cavity in a sensor is described in detail in U.S. Pat. No. 5,618,587 to Markle et al.; incorporated herein in its entirety by reference thereto. The first solution is allowed to fill the cavity 6 within the optical fiber 10.

In some embodiments, the first solution is aqueous and the monomer, the crosslinker and the first initiator are soluble in water. For example, in some embodiments, the monomer is acrylamide, the crosslinker is bisacrylamide and the first initiator is ammonium persulfate. In other embodiments, the monomer is dimethylacrylamide or N-hydroxymethylacrylamide. By increasing the concentrations of the monomer and/or crosslinker, the porosity of the resulting gel can be decreased. Conversely, by decreasing the concentrations of the monomer and/or crosslinker, the porosity of the resulting gel can be increased. Other types of monomers and crosslinkers are also contemplated. In other embodiments, the first solution further comprises an analyte indicator system comprising a fluorophore and an analyte binding moiety that functions to quench the fluorescent emission of the fluorophore by an amount related to the concentration of the analyte. In some embodiments, the fluorophore and analyte binding moiety are immobilized during polymerization, such that the fluorophore and analyte binding moiety are operably coupled. In other embodiments, the fluorophore and analyte binding moiety are covalently linked. The indicator system chemistry may also be covalently linked to the polymeric matrix.

In some embodiments, after the sensor 2 is filled with the first solution, the optical fiber 10 and the first solution filled porous membrane sheath 14 and cavity 6 are transferred to and immersed into a second solution comprising a second initiator. In some embodiments, the second solution is aqueous and the second initiator is tetramethylethylenediamine (TEMED). In some embodiments, the second solution further comprises the same fluorescent dye and/or quencher found in the first solution and in substantially the same concentrations. By having the fluorescent dye and quencher in both the first solution and the second solution, diffusion of fluorescent dye and quencher out of the first solution and into the second solution can be reduced. In some embodiments where a second solution is used, the second solution further comprises monomer in substantially the same concentration as in the first solution. This reduces diffusion of monomer out of the first solution by reducing the monomer gradient between the first solution and the second solution.

In some embodiments, at or approximately at the interface between the first and second solutions, the first initiator and the second initiator can react together to generate a radical. In some embodiments, the first initiator and the second initiator react together in a redox reaction. In other embodiments, the radical can be generated by thermal decomposition, photolytic initiation or initiation by ionizing radiation. In these other embodiments, the radical may be generated anywhere in the first solution. Once the radical is generated, the radical can then initiate polymerization of the monomer and crosslinker in the first solution.

When the radical is generated via a redox reaction as described herein, the polymerization proceeds generally from the interface between the first and second solutions to the interior of the porous membrane sheath 14 and towards the cavity in the optical fiber 10. Rapid initiation of polymerization can help reduce the amount of first initiator that can diffuse from the first solution and into the second solution. Reducing the amount of first initiator that diffuses out of the first solution helps reduce polymerization of monomer outside the porous membrane sheath 14 which helps in forming a smooth external surface. Polymerization of the monomer and crosslinker results in a hydrogel 8 that in some embodiments substantially immobilizes the indicator system, forming the sensor 2. Further variations on polymerization methodologies are disclosed in U.S. Patent Publ. No. 2008/0187655; incorporated herein in its entirety by reference thereto.

With reference to FIG. 3A, in certain embodiments, the glucose sensor 2 is a solid optical fiber with a series holes 6A drilled straight through the sides of the optical fiber. In certain embodiments, the holes 6A are filled with the hydrogels 8. In certain embodiments, the series of holes 6A that are drilled through the glucose sensor 2 are evenly spaced horizontally and evenly rotated around the sides of the glucose sensor 2 to form a spiral or helical configuration. In certain embodiments, the series of holes 6A are drilled through the diameter of the glucose sensor 2. With reference to FIG. 3B, in certain embodiments, the glucose sensor 2 is a solid optical fiber with a series of holes 6A drilled through the sides of the fiber at an angle. In certain embodiments, the series of holes 6A drilled at an angle, which are filled with hydrogel 8, are evenly spaced horizontally and evenly rotated around the sides the glucose sensor 2. With reference to FIG. 3C, in certain embodiments, the optical fiber comprises a groove 6B along the length of the optical fiber, wherein the groove 6B is filled with hydrogel 8. In certain embodiments, the depth of the groove 6B extends to the center of the optical fiber. In certain embodiments, the groove 6B spirals around the optical fiber. In certain embodiments, the groove 6B spirals around the optical fiber to complete at least one rotation. In certain embodiments, the groove spirals 6B around the optical fiber to complete multiple rotations around the optical fiber.

With reference to FIG. 3D, in certain embodiments, the glucose sensor 2 is a solid optical fiber with triangular wedges 6C cut from the fiber. In certain embodiments, the triangular wedge areas 6C are filled with hydrogel 8. In certain embodiments, the triangular wedges cut-outs 6C are evenly spaced horizontally and around the sides of the glucose sensor 2. In certain embodiments, all light traveling in the glucose sensor 2 is transmitted through at least one hole 6A or groove 6B filled with hydrogel 8.

In certain embodiments, as illustrated in FIG. 4, the glucose sensor 2 comprises an optical fiber 10 having a distal end 12, an atraumatic tip portion 134 having a proximal end 136 and a distal end 138, a cavity 6 between the distal end 12 of the optical fiber 10 and the proximal end 136 of the atraumatic tip portion 134, and a rod 140 connecting the distal end 12 of the optical fiber 10 to the proximal end 136 of the atraumatic tip portion 134. A hydrogel 8 containing glucose sensing chemistry, for example a fluorophore and quencher, fills the cavity 6. Covering the hydrogel filled cavity 6 is a selectively permeable membrane 14 that allows passage of glucose into and out of the hydrogel 8. Although these embodiments are described using a glucose sensor 2, it should be understood by a person of ordinary skill in the art that the sensor 2 can be modified to measure other analytes by changing, for example, the sensing chemistry, and if necessary, the selectively permeable membrane 14. The proximal portion of the sensor 2 comprises the proximal portion of the optical fiber 10. In some embodiments, the diameter, D1, of the distal portion of the sensor 2 is greater than the diameter, D2, of the proximal portion of the sensor 2. For example, the diameter D1 of the distal portion of the sensor 2 can be between about 0.0080 inches and 0.020 inches, while the diameter D2 of the proximal portion of the sensor 2 can be between about 0.005 inches to 0.015 inches. In some embodiments, the diameter D1 of the distal portion of the sensor 2 is about 0.012 inches, while the diameter D2 of the proximal portion of the sensor 2 is about 0.010 inches.

In some embodiments, the glucose sensor 2 includes a temperature sensor 25, such as thermocouple or thermistor. The temperature sensor 25 can measure the temperature of the hydrogel 8 and glucose sensing chemistry system. The temperature sensor 25 is particularly important when the glucose sensing chemistry, such as a fluorophore system, is affected by temperature change. For example, in some embodiments, the fluorescence intensity emitted by the fluorophore system is dependent on the temperature of the fluorophore system. By measuring the temperature of the fluorophore system, temperature induced variations in fluorophore fluorescence intensity can be accounted for, allowing for more accurate determination of glucose concentration, as more fully described below.

In certain embodiments, the hydrogels are associated with a plurality of fluorophore systems. In certain embodiments, the fluorophore systems comprise a quencher with a glucose receptor site. In certain embodiments, when there is no glucose present to bind with the glucose receptor, the quencher prevents the fluorophore system from emitting light when the dye is excited by an excitation light. In certain embodiments, when there is glucose present to bind with the glucose receptor, the quencher allows the fluorophore system to emit light when the dye is excited by an excitation light.

In certain embodiments, the emission produced by the fluorophore system varies with the pH of the solution (for example, blood), such that different excitation wavelengths (one exciting the acid form of the fluorophore and the other the base form of the fluorophore) produce different emissions signals. In preferred embodiments, the ratio of the emission signal from the acid form of the fluorophore over the emission signal from the base form of the fluorophore is related to the pH level of the blood; the simultaneous measurement of glucose and pH is described in detail in U.S. Patent Publication No. 2008/0188722 (incorporated herein in its entirety by reference thereto). In certain embodiments, an interference filter is employed to ensure that the two excitation lights are exciting only one form (the acid form or the base form) of the fluorophore.

Figure 5:
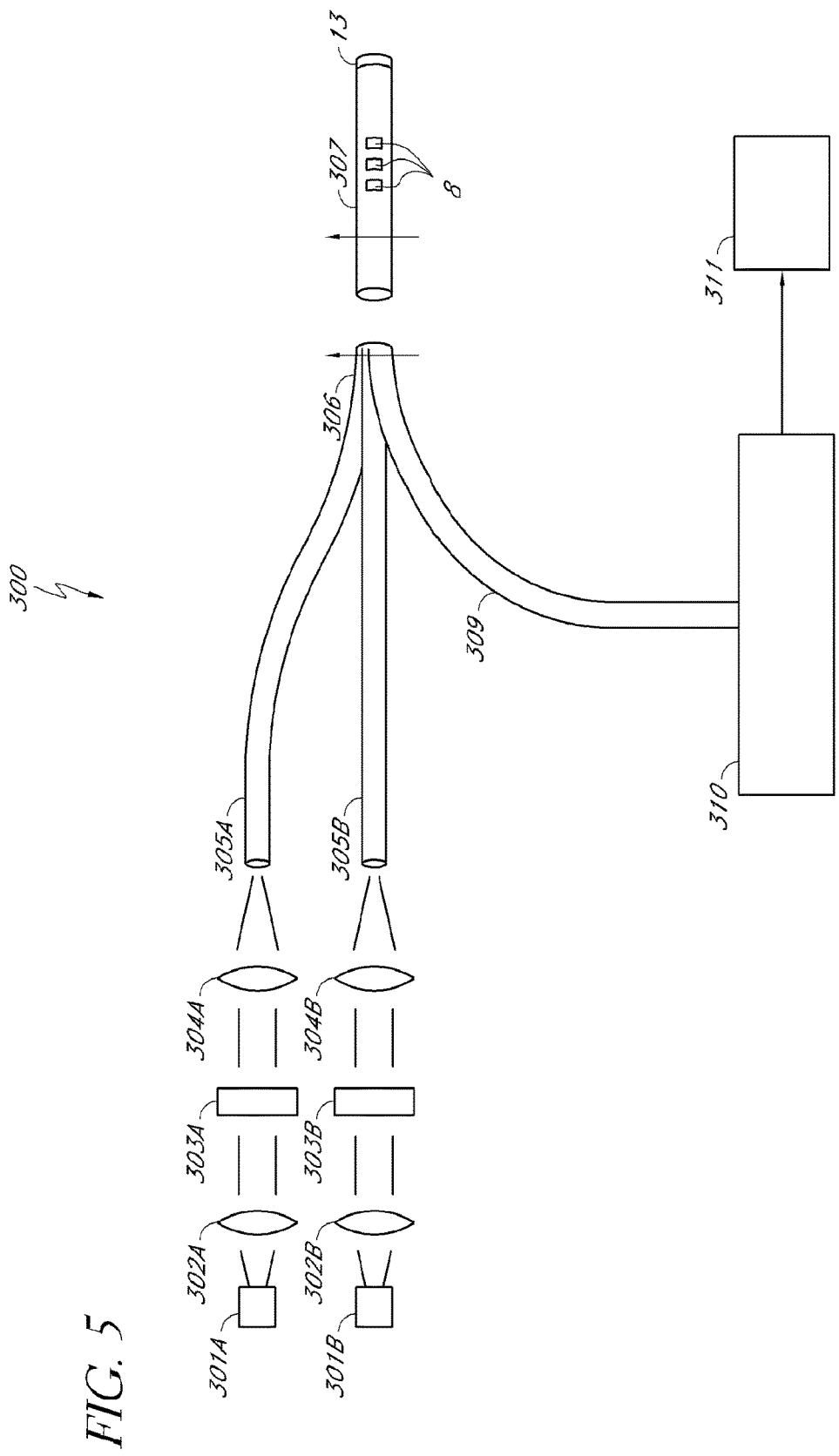
FIG. 5 shows a glucose measurement system comprising two excitation light sources and a microspectrometer and/or spectrometer.

Variations optical sensing systems, light sources, hardware, filters, and detection systems are described in detail in U.S. Publication No. 2008/0188725; incorporated herein in its entirety by reference thereto. See e.g., FIG. 5, wherein certain embodiments comprise at least two light sources. In certain embodiments, the light sources 301A, 301B generate excitation light that is transmitted through a collimator lens 302A, 302B. In certain embodiments, the resulting light from collimator lens 302A, 302B is transmitted to interference filters 303A, 303B. In certain embodiments, the resulting light from interference filters 303A, 303B is focused by focusing lens 304A, 304B into fiber optic lines 305A, 305B. In certain embodiments, fiber optic lines may be a single fiber or a bundle of fibers. In certain embodiments, the fiber optic line 309 may be a single fiber or a bundle of fibers. In certain embodiments, fiber optic lines 305A, 305B, 309 are bundled together at junction 306 and are connected at glucose sensor 307. The glucose sensor 307 comprises hydrogels 8.

In certain embodiments, the emission light and the excitation light are reflected off the mirror 13 and into the fiber optic line 309. In certain embodiments, the fiber optic line 309 is connected to microspectrometer 310 that measures the entire spectrum of light in the glucose measurement system 300. The microspectrometer 310 may be coupled to a data processing module 311, e.g., the sensor control unit and/or receiver/display unit. In certain embodiments, the ratio of emission light over the corresponding excitation light is related to the concentration of glucose. In certain embodiments, the ratio of the emissions light (for example, the acid form) produced by the first excitation light over the emission light (for example, the base form) produced by the second excitation light is related to pH levels in the test solution, for example blood.

In certain preferred embodiments, the microspectrometer is the UV/VIS Microspectrometer Module manufactured by Boehringer Ingelheim. Any microspectrometer can be used. Alternatively, the microspectrometer could be substituted with other spectrometer, such as those manufactured by Ocean Optics Inc.

In certain embodiments described above, the ratiometric calculations require measurements of various light intensities. In certain embodiments, these measurements are determined by measuring the peak amplitudes at a particular wavelength or wavelength band. In certain embodiments, these measurements are determined by calculating the area under the curve between two particular wavelengths as for example with the output from a microspectrometer.

With reference to FIGS. 6A and 6B, another embodiment of an intravascular optical glucose sensor is illustrated; this sensor configuration is disclosed in greater detail in WO2009/019470 (incorporated herein in its entirety by reference thereto). To provide a stronger and more robust sensor, which can withstand the pressures of being introduced into the body, yet retain some flexibility, sensors have been developed with internal reinforced walls, such as those depicted in FIGS. 6A and 6B. FIG. 6A shows a tube having a densely packed mesh 501A made of a first material and coated with an outer wall 502 of a second material. Three square cutouts 503 in the outer wall 502 of the tube arranged in a line can be seen in FIG. 6A, but cutouts of other shapes, positioned in other arrangements, are clearly feasible, depending on the embodiments. In the illustrated embodiment, the mesh 501A shows a high density of filament crossovers. This embodiment therefore has an increased strength and a reduced porosity. The braid is able to provide strength to the sensor, while allowing the tubular structure to flex and be maneuvered to the correct sensing position.

FIG. 6B depicts an embodiment in which the first material is in the form of a coil 501B which is coated with an outer wall 502 of the second material. Similar to FIG. 6A, three square cutouts 503 in the outer wall 502 of the tube arranged in a line can be seen in FIG. 6B, but cutouts of other shapes, positioned in other arrangements, are clearly feasible, depending on the embodiments. In this embodiment, the coil 501B is densely packed, providing increased strength and reduced porosity in a similar manner to the embodiment depicted in FIG. 6A. The reinforced walls can be provided in a number of ways, for example by providing a braided tubular structure which contains the sensing apparatus, as described in International patent publication WO2004/054438; incorporated herein in its entirety by reference thereto.

The first material is in the form of a mesh 501A, the density of filament crossovers may be varied in order to control the properties of the resulting tube. For example, a high density mesh may have greater strength and a low density mesh a greater flexibility. Variation in mesh density will also vary the porosity of the mesh. This is significant at the location of the opening in the outer wall since the porosity of the mesh will control the speed of diffusion of the material to be tested into the tube. Variation in the tightness of a coil can provide a similar effect.

The second material is used to coat the first material in order to form a continuous substantially impermeable outer wall 502 of the hollow tube. As used herein, the phrase substantially impermeable means that the second material forms an effectively closed tube, which is impermeable to the ingress of material from outside the tube to inside the tube. Accordingly, until a portion of the second material is removed, the tube is effectively sealed along its length, except, in some embodiments, at its ends.

Suitable materials for use as the second material generally include polymeric materials, more particularly polyesters, polyolefins such as polyethylene (PE), e.g. low density polyethylene (LDPE), fluoropolymers such as fluorinated ethylene propylene (FEP), polytetrafluoroethylene (PTFE) and perfluoroalkoxy polymer (PFA), polyvinylchloride (PVC), polyamides such as polyether block amide (PEBA), Pebax®, nylon and polyurethane. Polyesters and polyolefins are preferred due to their suitability for extrusion over the coil 501B or tubular mesh 501A. The selective removal of a portion of a polyester or polyolefin coating, e.g. by laser ablation, is also straightforward. Polyolefins are particularly preferred due to the ease of laser ablating these materials.

In order to form a continuous substantially impermeable tube prior to selective removal of a portion of the second material, the second material is first used to coat the coil or tubular mesh formed by the first material. The second material can either coat the outer surfaces of the first material, and in effect form a continuous substantially impermeable tube around the coil or tubular mesh formed by the first material, or the second material can entirely encapsulate the first material, effectively forming a tube of the second material in which is embedded the coil or tubular mesh formed by the first material. In one embodiment the second material can be applied to the first material by dip coating the coil or tubular mesh formed by the first material. In this embodiment, the second material is probably a polyamide, which results in a very stiff tube. In another embodiment, a tube of the second material can be provided, around which is formed the coil or tubular mesh of the first material. A further layer of the second material is then applied over the first material, resulting in the first material being sandwiched between two layers of the second material.

In a preferred embodiment, the first material is metallic and the second material is polymeric. In addition to the first and second materials, it is possible to include further materials in the tubes of the invention. For example, for some applications it may be useful to include a radiopaque additive to enable the sensor incorporating the tube to be visible in vivo. For example, radiopaque additives such as barium sulfate, bismuth subcarbonate, bismuth trioxide and tungsten can be added. Where present, these are preferably doped within the second material.

In certain processes, a portion of the second material is selectively removed in order to generate at least one opening in a region of the outer wall, while retaining the first material in that region. As the first material is present in the form of a coil or a tubular mesh, the first material does not form a completely closed tube. Accordingly, when the second material is removed in said region, this effectively forms a break in the continuous substantially impermeable wall of the tube. Where the second material simply coats the first material, it is necessary simply to remove the coating provided by this second material in the region where the opening is to be formed. Where the second material effectively encapsulates the first material, it is necessary to remove all of the second material which surrounds and encapsulates the first material in the region where the opening is to be formed.

Preferably, the chemical indicator system of the sensor is located adjacent to the opening formed by selective removal of the second material. This allows sensing of the environment in the region of the opening on the tube wall. For example, where the sensor is a glucose sensor, glucose is able to pass from the blood vessel or other cavity where the sensor is introduced through the opening and into the tube where its presence can be detected and measured by the probe.

The size of the opening in the outer wall will generally be between 1 and 400 $mm^2$, for example between 25 and 225 $mm^2$. The size of the opening must not be too small otherwise the blood or other substance into which the sensor is introduced will not be able to pass through the opening or will pass through in insufficient quantities for an accurate measurement to be made. The opening must also be large enough to allow positioning of the probe such that it is adjacent to the opening, even if it moves slightly when the sensor is introduced into the body.

In one embodiment, only one opening is generated in the tube wall, i.e. only one region of the second material is selectively removed. Preferably the opening extends only a portion of the way around the circumference of the tube. In one embodiment, it is preferred to retain some continuity of the second material along the entire length of the tube, and is hence preferred that the opening does not extend fully around the circumference of the tube. For example, it may be preferred that the opening extends around up to a maximum 75%, more preferably up to 50%, of the circumference of the tube. In another embodiment of the invention, a plurality of openings can be generated in the tube wall, i.e. more than one region of the second material can be selectively removed. This embodiment allows for probes to be located at a number of points along the length of the tube, and for multiple measurements to be taken. Thus, it is possible for a number of probes to be located within the tube, each tube being adjacent to a different opening within the tube wall. Alternatively, a single probe could be located within the tube and be provided with means for moving it from one opening to another opening, hence allowing measurements to be taken at a number of points along the length of the tube.

Thromboresistant Coatings

Molecules of a biocompatible agent are attached to the surfaces of the medical device to improve biocompatibility, such as antithrombogenic agents like heparin, albumin, streptokinase, tissue plasminogin activator (TPA) or urokinase. For example, the biocompatible agent may comprise molecules of both albumin and heparin. In one embodiment the molecules of a biocompatible material are joined to one another to form a film that is attached to a solid surface by a linking moiety. In other examples, various surface treatments of the optical glucose sensor can be used, such as those disclosed in U.S. Pat. Nos. 4,722,906, 4,973,493, 4,979,959, 5,002,582, 5,049,403, 5,213,898, 5,217,492, 5,258,041, 5,512,329, 5,563,056, 5,637,460, 5,714,360, 5,840,190, 5,858,653, 5,894,070, 5,942,555, 6,007,833, 6,090,995, 6,121,027, 6,254,634, 6,254,921, 6,278,018, 6,410,044, 6,444,318, 6,461,665, 6,465,178, 6,465,525, 6,506,895, 6,559,132, 6,669,994, 6,767,405, 7,300,756, 7,550,443, 7,550,444, and U.S. Patent Publ. Nos. 20010014448, 20030148360, and 20090042742 (each of which is incorporated herein in its entirety by reference thereto).

In one embodiment, the chemical linking moiety has the formula A-X-B in which A represents a photochemically reactive group capable of bonding covalently to a solid surface; B represents a different reactive group capable desirably in response to specific activation to which group A is unresponsive, of forming a covalent bond to a biocompatible agent and X represents a relatively inert, noninterfering skeletal moiety joining groups "A", and "B", that is resistant to cleavage in aqueous physiological fluid. The physiological fluid referred to is such fluid with which X will come in contact (e.g., blood, interstitial fluid, etc.). In a method of the invention group "A" of the linking moiety is covalently bound to the solid surface, with a sufficient population density to enable the molecules of the biocompatible agent to effectively shield the solid surface when the molecules are covalently bound to group "B" to provide a biocompatible effective surface. A biocompatible device of this invention includes a solid surface to which molecules of a biocompatible agent have been bound via the chemical-linking moiety as follows: solid surface-A residue-X-B residue-molecules of a biocompatible agent.

In one embodiment, the molecules of the biocompatible agent are selectively bound to the solid surface with a sufficient population density to provide a biocompatible effective surface using a chemically linking moiety that has the formula:

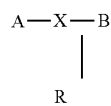

in which R represents a selector group that is a member of a specific bonding pair and that is reactive to form a bond with a receptor forming the other member of the specific binding pair and carried by a selected biocompatible agent and A, and B represent the groups described above as A and B. X represents a relatively inert, non-interfering skeletal radical joining groups "A", "B" and "R" and sterically enabling group "B" to separate from group "R" by at least about 10 Å.

Groups "B" and "R" are preferably sterically distinct groups; that is, they may, during the course of thermal vibration and rotation separate by a distance of at least about 10 Å. Group R, a "selector" group, representing a member of a specific binding pair, commonly forms a bond, usually noncovalent, with the biocompatible agent at an epitopic or other binding site of the latter (which site typifies a "receptor" herein). The group "B", which upon activation can covalently bond to the biocompatible agent, may be sterically spaced from the group "R", thereby enabling the covalent bond to be formed at a site spaced from the receptor site. In turn, the selector receptor bond may be disassociated from the receptor site through breakage of a fragile bond between the selector group and the chemical linking moiety followed by removal of the selector by, e.g., dialysis, environmental changes (pH, ionic strength, temperature, solvent polarity, etc.) or through spontaneous catalytic modification of the selector group (as when the biocompatible agent is an enzyme), etc. The receptor thus is reactivated to permit subsequent reaction with members of the specific binding pair.

As referred to herein, "specific binding pair" refers to pairs of substances having a specific binding affinity for one another. Such substances include antigens and their antibodies, haptens and their antibodies, enzymes and their binding partners (including cofactors, inhibitors and chemical moieties whose reaction the enzymes promote), hormones and their receptors, specific carbohydrate groups and lectins, vitamins and their receptors, antibiotics and their antibodies and naturally occurring binding proteins, etc. The concept of employing specific binding pairs in analytical chemistry is well known and requires little further explanation. Reference is made to Adams, U.S. Pat. No. 4,039,652, Maggio, et al, U.S. Pat. No. 4,233,402 and Murray, et al, U.S. Pat. No. 4,307,071, the teachings of which are incorporated herein by reference.

In certain embodiments, X is preferably a $C_1$-$C_{10}$ alkyl group such as polymethylene, a carbohydrate such as polymethylol, a polyoxyethylene, such as polyethylene glycol or a polypeptide such as polylysine.

The reactive group B is preferably a group that upon suitable activation covalently bonds to proteinaceous or other biocompatible agents. Such groups are typified by thermochemical groups and photochemical groups, as described and exemplified in Guire, U.S. Pat. No. 3,959,078, the teachings of which are incorporated herein by reference.

The photochemically reactive groups (A) (the covalent bonding of which is activated by actinic radiation) may be typified by aryl, alkyl and acyl azides, oxazidines, isocyanates (nitrene generators), alkyl and 2 ketodiazo derivatives and diazirines (carbene generators), aromatic ketones (triplet oxygen generators), aromatic diazonium derivatives and numerous classes of carbonium ion and radical generators. Reference is made to Frederick J. Darfler and Andrew M. Tometsko, chapter 2 of Chemistry and Biochemistry of Amino Acids, Peptides and Proteins (Boris Weinstein, ed) vol. 5, Marcel Dekker, Inc. New York, 1978, for further description of photochemically reactive groups. Azidonitrophenyls, fluoroazido nitrobenzenes, and aromatic ketones form a preferred group due to their stability to chemical reaction conditions in the dark and their susceptibility to activation by light of wave lengths harmless to most biomaterials, to form short-lived reactive intermediates capable of forming covalent bonds in useful yield with most sites on the biomaterial.

Nitrophenylazide derivatives (shown as including the X group) appropriate for use as photochemically reactive groups for the most part can be derived from fluoro-2-nitro-4-azidobenzene, and include 4-azido-2-nitrophenyl(ANP)-4-aminobutyryl, ANP-6-aminocaproyl, ANP-11-aminoundecanoyl, ANP-glycyl, ANP-aminopropyl, ANP-mercaptoethylamino, ANP-diaminohexyl, ANP-diaminopropyl, and ANP-polyethylene glycol. ANP-6-aminocaproyl, ANP-11-aminoundecanoyl, and ANP-polyethylene glycol are preferred. Aromatic ketones preferred for use as photochemically reactive groups include benzylbenzoyl and nitrobenzylbenzoyl.

Thermochemical reactive groups (that are activated by heat energy) are typified by and include nitrophenylhalides, alkylamino, alkylcarboxyl, alkylthiol, alkylaldehyde, alkylmethylimidate, alkylisocyanate, alkylisothiocyanate and alkylhalide groups.

Groups appropriate for use as thermochemically reactive groups include carboxyl groups, hydroxyl groups, primary amino groups, thiol groups, maleimides and halide groups. N-oxysuccinimide carboxylic esters of such groups as 6-amino hexanoic acid and amino undecanoic acid, alkylthiol groups such as mercapto succinic anhydride and beta-mercaptopropionic acid, homocysteinethiolactones, and polyetheylene glycol derivatives are preferred.

Other linking agents can also be used in the embodiments of the present disclosure, such as those disclosed in U.S. Pat. No. 6,077,698, which is incorporated herein by reference. For example, a chemical linking agent comprising a di- or higher functional photoactivatable charged compound can be used. The linking agent preferably provides at least one group that is charged under the conditions of use in order to provide improved water solubility. The linking agent may further provide two or more photoactivatable groups in order to allow the agent to be used as a cross-linking agent in aqueous systems. In preferred embodiments, the charge is provided by the inclusion of one or more quaternary ammonium radicals, and the photoreactive groups are provided by two or more radicals of an aryl ketone such as benzophenone.

The thromboresistant agent may carry one or more latent reactive groups covalently bonded to them. The latent reactive groups are groups which respond to specific applied external stimuli to undergo active specie generation with a resultant covalent bonding to an adjacent support surface. Latent reactive groups are those groups of atoms in a molecule which retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups as described are generally well known.

The azides constitute a preferred class of latent reactive groups and include arylazides, such as those disclosed in U.S. Pat. No. 5,002,582, which is incorporated by reference herein, for example phenyl azide and particularly 4-fluoro-3-nitrophenyl azide, acyl azides such as benzoyl azide and p-methylbenzoyl azide, azido formates such as ethyl azidoformate, phenyl azidoformate, sulfonyl azides such as benzenesulfonyl azide, and phosphoryl azides such as diphenyl phosphoryl azide and diethyl phosphoryl azide. Diazo compounds constitute another class of latent reactive groups and include diazoalkanes (—$CHN_2$) such as diazomethane and diphenyldiazomethane, diazoketones such as diazoacetophenone and 1-trifluoromethyl-1-diazo-2-pentanone, such as t-butyl diazoacetate and phenyl diazoacetates, and beta-ketone-alpha-diazoacetates such as t butyl alpha diazoacetoacetate. Other latent reactive groups include the aliphatic azo compounds such as azobisisobutyronitrile, the diazirines such as 3-trifluoromethyl-3-phenyldiazirine, the ketenes (—CH=C=O) such as ketene and diphenylketene and photoactivatable ketones such as benzophenone and acetophenone. Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate. Upon activation of the latent reactive groups to cause covalent bond formation to the surfaces to which polymer molecules are to be attached, the polymer molecules are covalently attached to the surfaces by means of residues of the latent reactive groups. Exemplary latent reactive groups are recited in U.S. Pat. No. 5,002,582 incorporated herein by reference.

The polymers and oligomers used may have one or more latent reactive groups. In certain embodiments, the polymers have at least one latent reactive group per molecule with the ratio of reactive groups extended polymer length, in Angstroms, ranging from about 1/10 to about 1/700 and preferably from about 1/50 to 1/400. As will be noted from the foregoing description, photoreactive latent reactive groups are for the most part aromatic and hence generally are hydrophobic rather than hydrophilic in nature.

The latent reactive groups and the polymer molecules to which they are bonded may have substantially different solvophilic properties. For example, the latent reactive groups may be relatively hydrophobic, whereas the polymer molecules may be relatively hydrophilic; when solution of the molecules is contacted with a relatively hydrophobic surface, it is believed that the latent reactive groups, being hydrophobic, tend to orient nearer the surface so as to improve bonding efficiency when the latent reactive groups are activated. The preferred latent reactive groups are benzophenones, acetophenones, and aryl azides.

The loading density of polymers upon a surface may be improved by a process in which a latent reactive molecule (a molecule having a latent reactive group) is first brought into close association (as by means of a solvent solution) to a surface, and thereafter the polymer to be bonded to the surface is brought into contact with and is covalently bonded to the latent reactive molecule, as to a reactive group different from the latent reactive group. Thereafter, the latent reactive groups may be activated to cause them to covalently bond to the surface to thereby link the polymers to the surface.

In other embodiments, polymer chains may be provided upon a surface or other substrate by first covalently bonding to the substrate through a latent reactive group a monomer, oligomer or other reactive chemical unit. To the thus bonded reactive units are covalently bonded monomers or oligomers in a polymerization reaction or polymers via covalent bonding (grafting) of the reactive units onto the polymer chains.

The reactive chemical units of the invention carry covalently bonded thereto latent reactive groups as described herein for covalent attachment to a non pretreated surface or other substrate. These molecules are characterized as having reactive groups capable of covalent bonding to polymer molecules of a polymer having the desired characteristics, or of entering into a polymerization reaction with added monomers or oligomers to produce polymer chains having the desired characteristics. Reactive chemical molecules capable of covalently bonding to polymer molecules include not only monomers and oligomers of various types but also molecules having such functional groups as carboxyl, hydroxyl, amino, and N-oxysuccinimide, such groups being reactive with reactive groups carried by the polymer chain to bond to the chain. The reactive chemical molecules are preferably monomers or oligomers and most preferably are ethylenically unsaturated monomers capable of entering into an addition polymerization reaction with other ethylenically unsaturated monomers. Particularly preferred are the acrylate and methacrylate monomers which are the esterification products of acrylic or methacrylic acid and hydroxy-functional latent reactive groups. Examples of such molecules include 4-benzoylbenzoyl-lysyl-acrylate.

Utilizing reactive chemical units bearing latent reactive groups, one may first coat a surface or other substrate with a solvent solution of such molecules. Upon removal of solvent, the application of an appropriate external stimulus such as U.V. light will cause the molecules to covalently bond, through the latent reactive groups, to the substrate. The substrate may then be appropriately contacted with a solution containing the desired polymer, monomer or oligomer molecules to cause bonding to these molecules. For example, if the reactive chemical unit molecule is carboxyl functional, it may be reactive with, and covalently bonded to, an appropriate hydroxyl-functional polymer such as dihydroxy polyethylene glycol. If the reactive chemical molecule is a monomer or oligomer, e.g., a methacrylate monomer, the substrate to which the molecule is covalently bonded may be contacted with a solution of addition-polymerizable monomers such as hydroxyethyl methacrylate and a free-radical addition polymerization initiator such as dibenzoyl peroxide under addition polymerization conditions to result in the growth of polymer chains from the monomer molecules bound covalently to the substrate. Once the desired polymerization has occurred, the substrate may be washed to remove residual monomer, solvent and non bound polymer that was formed.

In other embodiments the thromboresistant coating can adhere better by surface modification of the medical device by adsorbing a layer of a polyamine having a high average molecular weight on to the surface. The polyamine is stabilised by cross-linking with crotonaldehyde, which is a mono-aldehyde having a C—C double bond in conjugation with the aldehyde function. Thereafter one or more alternating layers of an anionic polysaccharide and the cross-linked polyamine, followed by a final layer of the said polyamine, not cross-linked, may be adsorbed onto the first layer of cross-linked polyamine, whereby a surface modification carrying free primary amino groups is achieved.

In certain embodiments, the thromboresistant coating is made by bringing the substrate into contact with an aqueous solution of the polyamine at pH 8-10, for example pH 9. The concentration of the initial polyamine solution will range from 1-10% by weight, especially 5% by weight, 1 ml of which may be diluted to a final volume of 500-2000 ml, especially 1000 ml. This final solution may also comprise from 100-1000 µl, especially 340 µl crotonaldehyde. Alternatively the substrate will be treated first with a solution of polyamine of said concentration and pH, and then with a solution of the crotonaldehyde of the said concentration and pH. The temperature is not critical, so it is preferred for the treatment to be at room temperature.

After rinsing with water, the substrate is treated with a solution of an anionic polysaccharide, containing from about 10 to about 500 mg, preferably about 100 mg of the polysaccharide in a volume of 1000 ml. This step is executed at a temperature in the range of 40°-70° C., preferably about 55° C. and pH 1-5, preferably about pH 3.

After another rinsing with water, these first steps may be repeated one or several times and finally, after having adsorbed a layer of polysaccharide, the substrate may be treated with a polyamine solution having a concentration 1-20 times, preferably 10 times, that mentioned above, at the said temperature and pH. The polyamine will preferably be a polymeric aliphatic amine, especially polyethylene imine having a high average molecular weight, but any polyamine having a high average molecular weight and carrying free primary amino groups may be used. The anionic polysaccharide will preferably be a sulfated polysaccharide. The aminated surface may optionally be further stabilized by reduction with a suitable reducing agent such as sodium cyanoborohydride. The modified surface according to present invention has free primary amino groups by which chemical entities may be bound either ionically or covalently. Also aldehyde containing chemical entities may be bound by formation of Schiff's bases, eventually followed by a stabilization reaction such as a reduction to convert the Schiff's bases to secondary amines. Further examples are disclosed in U.S. Pat. No. 5,049,403 which is hereby incorporated by reference in its entirety.

In certain embodiments, to provide a thromboresistant coating to the medical device, a composition is prepared to include a solvent, a combination of complementary polymers dissolved in the solvent, and the bioactive agent or agents dispersed in the polymer/solvent mixture. The solvent is preferably one in which the polymers form a true solution. The pharmaceutical agent itself may either be soluble in the solvent or form a dispersion throughout the solvent.

Due to the properties of materials frequently used on the outer surface of sensors, sensors can be difficult to coat with conventional anticoagulants, or anti-thrombogenics, e.g., heparin, to obtain a suitable anticoagulant coating, which is sufficiently stable, long-lasting, and active for preferred intravascular applications, and yet is sufficiently invisible to analytes of interest and non-interfering with the sensor chemistry to allow reliable and sufficiently long-lasting operation. Various issues can arise relating to the suitability of a particular coating including, for example, stability of the coating during manufacturing and handling of the sensor, resistance of the coating to removals during use, such as by solubilization, reaction, etc., resistance to diffusion through the coating of analytes of interest, and interaction between species in the coating and the sensor technology, whether by hydrolysis of detectable species from the coating or by other means.

Coating materials comprising heparin are preferred, but other polysaccharide and biologically derived materials and analogs can be utilized as well, either with heparin or in place of heparin. Preferred methods of applying the coating include application of a heparin-quaternary ammonium complex in isopropanol to a sensor wetted with water or water/surfactant under vacuum, but other suitable methods of applying a coating can also be successfully employed, such as application of a heparin-quaternary ammonium complex from combinations of solvents, such as non-polar solvents and polar solvents; sequential application of quaternary ammonium compound and heparin, such as to form a heparin-quaternary ammonium complex in-situ; covalently bonding heparin molecules to the surface of the sensor, including methods for attaching individual ends of heparin molecules to the surface such as described by Carmeda AB (Upplands Vasby, Sweden); and application of cross-linked forms of heparin or heparin with other compounds.

In certain embodiments, a coating of heparin or a heparin containing material can be applied to at least a portion of the sensor surface to limit or prevent thrombus formation. However, in some cases, application of such a coating can be difficult due to problems of adhesion where the coating will not properly adhere to the surface initially or will tend to detach or dissolve from the surface upon use. Instances where the coating detaches upon use can be particularly problematic due to the possibility of particulate impurities being released into the bloodstream and the possibility that these can result in plugging of small blood vessels. In addition, detachment or dissolution of heparin coating material can result in therapeutic or sub-therapeutic dosing of the patient with an anticoagulant material. Such adhesion problems can be particularly pronounced when applied to certain types of materials, especially plastics such as polyolefins, fluoropolymers, polycarbonate, and polysulfone. For example, polyolefins and fluoropolymers in particular are especially difficult to adhere materials to, as evidenced by the difficulty and limited strength that is typically achieved when these plastics are glued.

The present inventors have found that surprisingly a coating comprising heparin and benzalkonium can be effectively applied and will maintain an acceptably stable and active coating over polymeric surfaces of analyte sensors disclosed herein, including polymeric surfaces such as polyolefins, fluoropolymers, polycarbonate and polysulfone, porous polymeric surfaces, and porous polymeric surfaces on sensors incorporating immobilizing polymeric matrices, while still maintaining acceptable functionality of the analyte sensor. In certain embodiments, the porous surfaces capable of maintaining an acceptably stable and active coating comprising heparin and benzalkonium are more specifically described as microporous, nanoporous, or mesoporous.

In preferred embodiments, the coating comprising heparin and benzalkonium may include pharmaceutical grade heparin, such as heparin sodium or heparin calcium as described in the U.S. Pharmacopeia, revised Jun. 18, 2008, however, other grades and forms of heparin can be utilized in various applications, including instances where pharmaceutical regulations do not apply. Preferred grades of heparin can have an average molecular weight of about 12 to about 15 kDa, however, individual strands can have molecular weights as high as about 40 kDa or 50 kDA or even higher, and as low as about 5 kDa or 3 kDa or even lower. In other embodiments, heparin with average molecular weights higher or lower than about 12 to about 15 kDa can be successfully utilized, such as those as high as about 20 or 30 kDa or as low as about 7 or 10 kDa.

In some preferred embodiments, the coating comprising heparin and benzalkonium may include molecules of benzalkonium chloride having alkyl groups of about 1 to about 5 carbons for two of the R-groups and an alkyl group of about six to about 22 carbons for the third R-group, either as a single pure compound or as a combination of compounds with differing R-groups. In some embodiments, grades of benzalkonium chloride include those having compounds and mixtures of compounds having primarily two methyl groups and an alkyl group of about six to about 22 carbons, or more preferably two methyl groups and an alkyl group of about 10 to about 18 carbons as the R-groups.

In certain embodiments, other ammonium complexes can be used, e.g., particular alkylbenzyl dimethyl ammonium cationic salts, which can be used in high loading concentrations with heparin to form coatings, as disclosed in U.S. Pat. No. 5,047,020 to Hsu; incorporated herein in its entirety by reference. Hsu found that commercially available benzalkonium chloride may comprise a mixture of alkylbenzyldimethylammonium chloride of the general formula, $[C_6H_5CH_2N(CH_3)_2R]Cl$, in which R represents a mixture of alkyls, including all or some of the groups comprising C8 and greater, with C12, C14 and C16 comprising the major portion. Generally, the composition breaks down to more than 20% C14, more than 40%, C12 and a less than 30% mixture of C8, C10 and C16. In contrast, Hsu found that preferred heparin/quaternary ammonium complexes have at least about 50 weight percent of the organic cationic salt, and preferably from 60 to 70 weight percent. Hsu found that optimum results were achieved with complexes consisting of cetalkonium heparin and/or stearylkonium heparin and mixtures thereof. Indeed, Hsu teaches that coatings for medical devices consisting of complexes of cetalkonium heparin and/or stearylkonium heparin and mixtures thereof, exhibit "vastly superior hydrophobicity and surface adhesion over the presently and most commonly used complexes of heparin and benzalkonium chloride." Accordingly, in another aspect of the invention, other heparin/quaternary ammonium complexes besides those comprising benzalkonium, like those disclosed by Hsu, may be used to coat and render thromboresistant the glucose sensors disclosed herein.

Surface Coating Agents

Various compounds can be useful as coating agents for the thromboresistant coating of the medical device, for example those disclosed in U.S. Pat. Nos. 6,278,018, 6,603,040, 6,924,390, 7,138,541, which are all incorporated herein by reference. In one aspect, the present invention provides a compound comprising a nonpolymeric core molecule comprising an aromatic group, the core molecule having attached thereto, either directly or indirectly, one or more substituents comprising negatively charged groups, and two or more photoreactive species, wherein the photoreactive species are provided as independent photoreactive groups. The first and second photoreactive species of the present coating agent can, independently, be identical or different.

In certain embodiments the core is provided as the residue of a polyhydroxy benzene starting material (e.g., formed as a derivative of hydroquinone, catechol, or resorcinol), in which the hydroxy groups have been reacted to form an ether (or ether carbonyl) linkage to a corresponding plurality of photogroups. In one embodiment, a coating agent of this invention further comprises one or more optional spacers that serve to attach a core molecule to corresponding photoreactive species, the spacer being selected from radicals with the general formula: wherein n is a number greater or equal to 1 and less than about 5, and m is a number greater or equal to 1 and less than about 4.

In another embodiment, such coating agents are selected from the group 4,5-bis(4-benzoylphenylmethyleneoxy)benzene-1,3-disulfonic acid di(potassium and/or sodium) salt, 2,5-bis(4-benzoylphenylmethyleneoxy)benzene-1,4-disulfonic acid di(potassium and/or sodium) salt, 2,5-bis(4-benzoylphenylmethyleneoxy)benzene-1-sulfonic acid monopotassium and/or monosodium salt.

Suitable core molecules of the present invention include nonpolymeric radicals having a low molecular weight (e.g., 100-1000 MW). Suitable core molecules provide an improved combination of such properties as coating density, structural stability, ease of manufacture, and cost. Further, core molecules can be provided with water soluble regions, biodegradable regions, hydrophobic regions, as well as polymerizable regions. Examples of suitable core molecules include cyclic hydrocarbons, such as benzene and derivatives thereof.

The type and number of charged groups in a preferred coating agent are sufficient to provide the agent with a water solubility (at room temperature and optimal pH) of at least about 0.1 mg/ml, and preferably at least about 0.5 mg/ml, and more preferably at least about 1 mg/ml. Given the nature of the surface coating process, coating agent solubility levels of at least about 0.1 mg/ml are generally adequate for providing useful coatings of target molecules (e.g., polymer layers) on surfaces.

The coating agent can thus be contrasted with many coating agents in the art, which are typically considered to be insoluble in water (e.g., having a comparable water solubility in the range of about 0.1 mg/ml or less, and more often about 0.01 mg/ml or less). For this reason, conventional coating agents are typically provided and used in solvent systems in which water is either absent or is provided as a minor (e.g., less than about 50% by volume) component.

Examples of suitable charged groups include salts of organic acids (e.g., sulfonate, phosphonate, and carboxylate groups), as well as combinations thereof. A preferred charged group for use in preparing coating agents of the present invention is a sulfonic acid salt, e.g., derivatives of $SO_3^-$ in which the counterion is provided by the salts of Group I alkaline metals (Na, K, Li ions) to provide a suitable positively charged species.

The use of photoreactive species in the form of photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultravieolet light-induced exitation of the benzophenome group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

Coating Methodology

The coating processes disclosed herein include: 1) direct coating of the heparin complex by straight application, as in the case of dip coating, as well as 2) indirect coating, as in the case of sequential applications of a quarternary ammonium salt plus surfactant and the ionic heparin. Suitable methods for applying a coating comprising heparin and benzalkonium may include multistep layering techniques as well as single step application of heparin complexes. In other embodiments, pretreatment methods are used, such as soaking the sensors in sodium heparin solutions.

In the event that it is desired to apply the thromboresistant coating to surfaces that are inert to certain polymeric materials, adhesion can be facilitated by chemically treating the surfaces in order to provide hydroxyl groups on or near the surface thereof. Exemplary chemical surface treatments in this regard include such known procedures as chemical etching, surfactant adsorption, coextrusion, plasma discharge, surface oxidation or reduction, radiation activation and oxidation, and surface grafting with materials such as polyvinyl alcohol, poly(2-hydroxyethyl methacrylate) and the like. Bulk modifications of the substrate surface can also be accomplished in order to provide active hydrogens. Examples of conventional modifications of this type include blending with polymers having active hydrogens, partial degradation of polymers, end group modification, monomer functionalization, oxidation, reduction, copolymerization, and the like.

In certain embodiments, a three-dimensional highly cross-linked matrix containing aminosilanes is formed on the medical device surface. The aminosilane is cured, cross-linked or polymerized in place on the surface to be rendered thromboresistant. This is carried out in a manner such that a three-dimensional matrix is formed. The matrix can be either an aminosilane homopolymer or a copolymer, including a graft copolymer, of an aminosilane with another silane that is not an aminosilane. Representative aminosilanes include 3-aminopropyltrimethoxysilane, 3-aminopropyltriethoxysilane, 2-aminoundecyltrimethoxysilane, aminophenyltrimethoxysilane, N-(2-aminoethyl-3-aminopropyl) trimethoxysilane, and trimethoxysilylpropyldiethylenetriamine.

Aminosilanes of this type can be used alone in order to form a homopolymer matrix. For example, certain aminosilanes are trifunctional and provide a highly crosslinked matrix. The hydrophilicity can be reduced, when desired, by combining the hydrophilic aminosilane with a less hydrophilic silane that is not an aminosilane. In one embodiment, a matrix that is a copolymer of one of these aminosilanes with another silane molecule that is not an aminosilane and that is less hydrophilic than an aminosilane in order to thereby adjust the hydrophilicity of the matrix. Other methods and coating agents are also known in the art, including U.S. Pat. Nos. 5,053,048, 4,973,493, 5,049,403, all of which are incorporated by reference herein.

In preferred embodiments, a coating comprising heparin and benzalkonium is applied by first wetting the sensor surface with water or a combination of water and surfactant. Preferred surfactants include anionic surfactants, however other surfactants such as cationic surfactants or non-ionic surfactants may also be successfully employed in some embodiments. In particular, suitable surfactants include sodium laurel sulfate, sodium dodecyl sulfate, ammonium lauryl sulfate, sodium laureth sulfate. The wetted sensor is then treated with an alcoholic solution of heparin-quaternary ammonium complex. In certain embodiments, the alcoholic solution comprises isopropanol, however other alcohol based solutions may be used as well, depending on the embodiment. Preferred solutions of isopropanol may include about 1 to about 99% (wt.) of heparin-benzalkonium complex in isopropanol, including 5%, 10%, 25%, 50%, 75%, 90%, and 95% (and also including ranges of weight percentages bordered on each end by these recited weight percentages). One preferred solution of heparin-benzalkonium in isopropanol is manufactured by Celsus Laboratories, Inc. 12150 Best Place, Cincinnati Ohio 45241, under product number BY-3189 (described as Benzalkonium heparin solution in isopropyl alcohol, 887 U/mL). The wetted sensor can be dipped in the heparin-benzalkonium solution, or it can be sprayed onto the surface of the sensor or applied by another suitable technique. The sensor with coating solution applied is then dried. Additional coating material, such as to improve consistency of a coating or to thicken a coating, can be applied by dipping, spraying or other suitable means. When material is applied, preferred methods include those where the sensor is exposed to the heparin-benzalkonium solution for only a limited time, such as less than one minute, or less than about 30 seconds or about 10 seconds or even about 1 or 2 seconds, such as by dipping the sensor into the solution for only about a second (and also including time intervals bordered on the high end and the low end by the recited durations such as dipping the sensor into the solution for between 10 and 30 seconds). In some embodiments, short time intervals can prevent undesirable results, such as excessive solubilization of material from the sensor surface or excessive dehydration of the sensor. However, in some embodiments, longer time periods can successfully be utilized by, for example, increasing the concentration of heparin-benzalkonium concentration of the solution or by supplementing the solution with additional benzalkonium material or heparin material, or by adjusting the pH, or ionic strength of the solution. In some embodiments, during the coating process, the sensor can be rehydrated as needed or desired by application of water or a combination of water and surfactant and/or solvent.

However, other methods of applying a coating comprising heparin and benzalkonium can also be successfully employed. Suitable multistep layering techniques include those techniques where an heparin and benzalkonium are applied by a process comprising application of a suitable form and grade of benzalkonium chloride followed by application of a suitable form and grade of heparin. Any suitable solvent or combinations of solvents can be used for heparin, such as water or aqueous alcohol, and for benzalkonium chloride, such as nonpolar organic solvents (for example, toluene, petroleum ether, etc.). Preferred heparin solutions include those comprising heparin in a weight percentage of about 0.05%, 1%, 5%, 10%, 25%, 50%, 75%, 90%, and 95% (and also including ranges of weight percentages bordered on each end by these recited weight percentages). In certain such embodiments, a preferred heparin solution comprises a weight percent of heparin between about 0.05% to about 1%. Preferred benzalkonium chloride solutions include those comprising benzalkonium in a weight percentage of about 0.05%, 1%, 5%, 10%, 20%, 25%, 50%, 75%, 90%, and 95% (and also including ranges of weight percentages bordered on each end by these recited weight percentages). In certain such embodiments, a preferred benzalkonium chloride solution comprises a weight percent of benzalkonium chloride between about 1.0% to about 20%.

Other suitable coating techniques are described, for example, in U.S. Pat. No. 3,846,353, to Grotta, and U.S. Pat. No. 5,047,020, to Hsu, incorporated by reference herein in their entireties.

Single step application of heparin complexes can comprise applying a solution comprising heparin and benzalkonium of a suitable grade and form to the sensor, such as is described in U.S. Pat. No. 5,047,020, to Hsu. In certain embodiments, the solution may include benzalkonium chloride. Suitable solvents for the heparin and benzalkonium include those comprising polar organic solvents, alone or as mixtures, such as alcohols (e.g. isopropanol), halogenated solvents (e.g. trifluoro-trichloro ethane), etc. In some embodiments, the solution to be applied to the polymeric surface may include heparin and benzalkonium in a combined weight percentage of 0.1%, 1%, 5%, 10%, 25%, 50%, 75%, or about 90% of the total weight of the solution (also including ranges of weight percentages bordered on each end by these recited weight percentages). In certain such embodiments, a solution may contain between about 0.1% to about 75% heparin/benzalkonium by weight. In some embodiments, successive layers of heparin/benzalkonium complex can be applied to the surface of the sensor, for example, to build up a coating having a desired thickness and/or durability.

In certain embodiments, the distal portion of a pre-wetted sensor is dipped in a solution comprising heparin and benzalkonium in isopropanol, preferably for about 0.1 to about 30 seconds, and more preferably for about 1 to about 10 seconds, and even more preferably for about 1 second. In certain embodiments, the dipped sensor is subsequently air dried, preferably for at least about 10 seconds, and more preferably for about 0.5 minutes to about 10 minutes, and even more preferably for about 1 minute. The heparin/benzalkonium coating and drying steps are repeated in accordance with various embodiments, preferably from about 1 to about 20 times, or more preferably from about 2 to about 10 times, or even more preferably from about 3 to about 8 times, and even more preferably still from about 4 to about 6 times.

In certain embodiments, a sustained release of heparin from the sensor surface into the surrounding vessel is achieved by soaking the sensor. In one embodiment, the sensor, which optionally contains a hydrogel underneath the optional microporous membrane, is soaked in a solution of heparin for infusion of heparin into the swollen hydrogel. In one embodiment, an aqueous solution of at least about 10% sodium heparin is used. In a more preferred embodiment, an aqueous solution of at least about 20% sodium heparin is used. In a most preferred embodiment, an aqueous solution of at least about 30% sodium heparin is used. In other embodiments, other organic solvents and other forms of heparin may be used. In one embodiment, the sodium heparin solution is in phosphate buffered saline of about pH 5. After soaking for enough time to saturate the hydrogel, the sensor is removed from the solution and allowed to dry. In one embodiment, the sensor is soaked for at least about 1 hour. In a preferred embodiment, the sensor is soaked for about 2 hours. In one embodiment, the sensor is soaked for at least about 3 hour. When the sensor is then deployed in-vivo, the hydrogel re-swells in the bloodstream thus releasing the heparin gradually over time.

Additional steps can be utilized as necessary, such as, for example, cleaning the surface of the sensor with suitable agents such as solvents, surfactants, etc. and/or drying the coating, such as with a gas stream, or with heat, or with a heated gas stream, or with one or more dehydrating agents. In some embodiments, it is desirable to package the sensor as soon as possible after coating, since in some embodiments, after coating, the surface of the sensor may be somewhat tacky, and it may tend to pick up particulate matter.

Other methods of applying a heparin-based coating to the sensor includes covalently bonding heparin, or a heparin derivative, to the surface of the sensor or to an intermediate material applied to the surface of the sensor. Suitable techniques include those that covalently bond the end of a heparin molecule to the surface of the sensor or an intermediate, such as the techniques utilized by Carmeda AB (Upplands Vasby, Sweden). Other suitable methods also include those utilizing photoimmobilization to attach heparin, or a heparin derivative to the surface of a sensor or an intermediate material applied to the surface of the sensor, such as are described herein and by Surmodics (Eden Prairie, Minn.), as well as those depositing heparin complexes with polar and nonpolar solvents, such as are described in U.S. Pat. No. 6,833,253 to Roorda, et al.

WORKING EXAMPLES

Example 1

Application of Thromboresistant Coating

An optical glucose sensor as described above (see e.g., FIGS. 1-4) was prepared for coating with benzalkonium/heparin by immersing the portion of the sensor to be coated in a pH 3 phosphate buffered saline solution (although it is feasible to use many types of aqueous buffer solutions or even just water).

A coating solution of 1.5% (by weight) benzalkonium heparin in isopropanol (distributed by Celsus Laboratories, Inc. 12150 Best Place, Cincinnati Ohio 45241 as Benzalkonium heparin solution in isopropyl alcohol, 887 U/mL, Product Number BY-3189) was added to a test tube. After equilibrating in the buffered saline solution, the distal end portion of the sensing end of the sensor was immersed in the benzalkonium heparin solution and immediately removed (with the time of immersion in the benzalkonium heparin solution being approximately one second). The wet sensor was allowed to air dry for approximately 1 minute, resulting in a coating of benzalkonium heparin on the sensor surface.

Immersion of the sensor in the benzalkonium/heparin solution followed by air drying was repeated 4 times to build up additional coating material on the surface of the sensor.

Example 2

Preparation of Sensor Blank

A sensor blank was prepared from a polyethylene microporous membrane (of 0.017 inch outside diameter) surrounding a poly(methyl methacrylate) optical fiber (of 0.010 inch diameter). The polyethylene microporous membrane was obtained from Biogeneral 9925 Mesa Rim Road, San Diego Calif. 92121-2911). The distal end of the sensor blank (the end to be coated) is heat welded to a rounded polyethylene plug. The other end is sealed with a silicone backfill. The distal end was then immersed in the buffered saline solution of Example 1 for about 18 hours (although a shorter time interval would also have been suitable). Finally, the distal end of the sensor blank was immersed in the coating solution of Example 1 and subsequently air dried as in Example 1. The steps of immersing in the coating solution and air drying were repeated four times.

Example 3

Comparison of Coated Sensor and Coated Sensor Blank

Coated sensors and coated sensor blanks, prepared as described in Examples 1 and 2, each having five dip coats of heparin/benzalkonium applied, were subjected to handling tests as follows.

Sensors consisted of a 1.3-inch long hollow, microporous High Density Polyethylene (HDPE) membrane (0.017 inches O.D., Biogeneral 9925 Mesa Rim Road, San Diego Calif. 92121-2911, this is a custom part) butt-welded to a 1.0-inch long, smooth (nonporous) HDPE tube. The microporous end was heat-welded to a rounded polyethylene plug. Inside of the hollow assembly was threaded a 0.010 inch PMMA optical fiber The smooth HDPE end was filled with silicone backfill up to, but not including, the microporous membrane. The area between the PMMA optical fiber and the hollow microporous membrane was filled with a dimethyl acrylamide gel which also contained covalently-bound fluorescent dye and quencher. The sensor was prepared for application of the coating comprising heparin and benzalkonium by immersing the distal ("sensor") end in an aqueous solution of phosphate buffered saline as described in Example 1 for about 18 hours (although this amount of time may not be necessary). The sensor was then immersed in the heparin/benzalkonium solution and air dried as described in Example 1. The immersion and drying steps were repeated 4 times.

After repeated immersions in the coating solution and drying, the sensors and sensor blanks were prepared for the handling tests by staining with toluidine blue. Specifically, the sensors and sensor blanks were pulled through the silicone rubber seal, and then dipped in a 0.04% solution of toluidine blue in water for 1 minute, rinsed with water and allowed to air dry for 30 minutes.

Toluidine blue stains heparin a purple color, and so a darker purple color tends to indicate a higher concentration of heparin than a lighter purple color or no purple color at all. Thus, in order to assess the durability of the heparin coating, the stained sensors and sensor blanks were subjected to the following handling tests and subsequently visually examined under 20x magnification to discern voids and thinness in the heparin coating indicated by the lightening of the toluidine stain. The results are described below as well.

Storage in Phosphate Buffered Saline Solution

Sensors were soaked in pH 7.4 phosphate buffered saline for up to 48 hours at 37 C. Microporous membrane sections were observed to retain an even purple color even after 48 hours. The stain on nonporous polyethylene sections became lighter and less even after as little as 2 hours.

Storage in Sensor Housing Assembly

A coated sensor was placed into a sensor housing assembly, consisting of a polyurethane tubing and sealed with a parylene-coated silicone rubber seal. The housing assembly was filled with pH 7.4 phosphate buffered saline and the sensor was soaked in the housing for 1 hour at room temperature. Afterwards, the nonporous polyethylene section displayed (under magnification) clear signs of damage to the heparin coating, with apparent scrapes and voids in the purple stain. In contrast, the microporous membrane section looked unaffected, with a consistent and smooth purple stain. Abrasion: A sensor was soaked in pH 7.4 phosphate buffered saline for 1 hour at room temperature, then rubbed vigorously with a wet nitrile glove for one minute. It was then stained with toluidine blue. Under magnification, the nonporous polyethylene section was almost completely devoid of purple stain, indicating a total loss of the heparin coating. The microporous membrane section looked to be diminished and somewhat patchy, although there was still a strong purple color along the entire length. It should be noted that the handling in this portion of the test was very extreme.

Sonication with Isopropanol

Figure 7A:
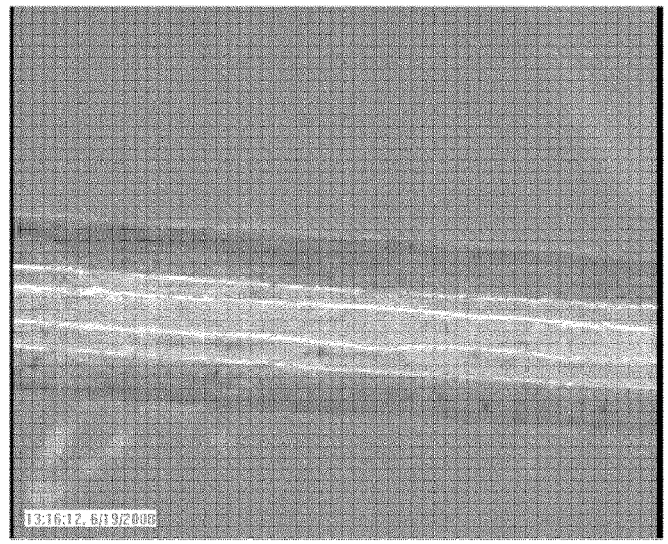
FIG. 7A illustrates the adhesion of a coating of heparin benzalkonium to a microporous membrane section of a sensor.
Figure 7B:
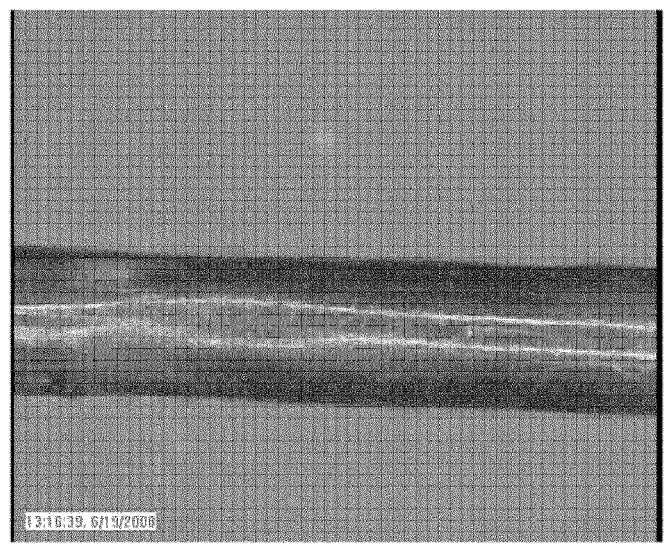
FIG. 7B illustrates the adhesion of a coating of heparin benzalkonium to a nonporous precursor section of a sensor.

One sensor was sonicated three times in successive vials of 25 mLs isopropanol for 5 minutes each. It was then stained with toluidine blue. Under magnification, the nonporous precursor polyethylene section was almost completely devoid of purple stain, indicating total loss of the heparin coating, as shown in FIG. 7A. The microporous membrane section still maintained a strong, even purple color, indicating that a consistent heparin coating remained, as shown in FIG. 7B.

The results of subjecting the sensors and blanks to the foregoing conditions are summarized in the following table:

| Test condition | Microporous membrane stain | Nonporous polyethylene stain |
|---|---|---|
| Storage in phosphate buffered saline solution | Dark, even purple stain | Lighter color, less even |
| Storage in sensor housing assembly | Dark, even purple stain | Clear signs of abrasion, large voids in purple stain |
| Abrasion | Lighter purple stain, still evenly coated | Purple stain completely removed |
| Sonication with isopropanol | Lighter purple stain, still evenly coated | Purple stain completely removed |
| Control (no handling tests) | Dark, even purple stain | Dark, even purple stain |

These results demonstrate the superior durability of the benzalkonium heparin coating on the glucose sensor, having a porous polymeric surface and hydrophilic polymer matrix, as compared in benzalkonium heparin coating on a polymeric surface alone.

Example 4

Demonstration of Effectiveness of Antithrombotic Coating

12 GLUCATH® sensors with a benzalkonium/heparin coating and 12 BD L-Cath PICC lines (outside diameter 0.037 cm, 0.0145 inches; polyurethane) as controls without coating were prepared for insertion into the cardiovascular system of four sheep. The coated GluCath sensor was constructed of a fluorophore/quencher indicator system embedded in a hydrophilic acrylic matrix, as described in U.S. patent application Ser. No. 12/026,396. The benzalkonium heparin coating was applied as described in Example 3.

Sensors and control catheters were inserted into the left and right jugular veins and left and right cephalic veins, with the sensor on one side and the control catheter on the other of the same sheep. After 25 hours, two sheep were euthanized and the sensors and controls were surgically exposed and examined by incising and reflecting the skin and surrounding tissues overlying the test article and vein, and then opening the vein longitudinally taking care not to disturb the sensor or catheter or any cellular accumulation or debris on the test articles or in the veins. After 22 additional hours (47 hours elapsed time), two additional sheep were euthanized and the sensors surgically exposed and examined as described above.

Digital photographs of each sensor or catheter were taken in place. After examination, each sensor or catheter was removed from the vein, stained with methylene blue, and examined microscopically at 10-20× primary objective power to observe build up of fibrin or cellular material or surface irregularities the low the resolution of the photographs. Two of the test articles were found to have been placed outside of the vein, in the surrounding tissue, and were not included in the evaluations.

Tissue sections from the veins were also obtained and characterized for the state of the vessel in proximity to the test articles. The results of these evaluations are shown in the table below:

| Sensor/Article | Time (Hr) | Sheep | Vessel | Fibrin buildup on sensor (gross assessment) | Fibrin buildup on sensor (microscopic assessment) | Vessel Wall | Notes |
|---|---|---|---|---|---|---|---|
| 4-GluCath | 25 | 193/24 | LJS | 0 | 0 | NGHL | — |
| 5-GluCath | 25 | 193/24 | LJI | NA* | NA | NGHL | *Sensor not in vessel, tip of sensor kinked. |
| 6-GluCath | 25 | 193/24 | LC | 0 | 0 | Focal microscopic endothelial erosion, with minor fibrin deposition | Tip of sensor kinked. |
| 7-GluCath | 25 | 196/25 | RJS | 0 | 0 | NGHL | — |
| 8-GluCath | 25 | 196/25 | RJI | 0 | 1 (equivocal) | NGHL | — |
| 9-GluCath | 25 | 196/25 | RC | 0 | 0 | Focal microscopic endothelial erosion, with minor fibrin deposition | — |
| 1-BD-LC | 25 | 193/24 | RJS | 1 | 1 | NGHL | — |
| 2-BD-LC | 25 | 193/24 | RJI | 0** | 0 | NGHL | **Most of sensor inadvertently pulled from vessel during dissection. This may have stripped some surface deposits off the catheter surface. |
| 3-BD-LC | 25 | 193/24 | RC | 1 | 1 | NGHL | — |
| 10-BD-LC | 25 | 196/25 | LJS | 1 | 1 | NGHL | — |
| 11-BD-LC | 25 | 196/25 | LC | 1 | 1 | NGHL | — |
| 12-GluCath | 47 | 194/27 | RJS | 0 | 0 | NGHL | — |

| Sensor/Article | Time (Hr) | Sheep | Vessel | Fibrin buildup on sensor (gross assessment) | Fibrin buildup on sensor (microscopic assessment) | Vessel Wall | Notes |
|---|---|---|---|---|---|---|---|
| 13-GluCath | 47 | 194/27 | RJI | 0 | 0 | NGHL | Tip of sensor is elongated and kinked. |
| 14-GluCath | 47 | 194/27 | RC | 0 | 0 | Mass of fibrin on vessel wall at tip of sensor, endothelium intact. | Tip of sensor kinked. |
| 20-GluCath | 47 | 195/26 | LJS | 0 | 0 | NGHL | — |
| 21-GluCath | 47 | 195/26 | LJI | 0 | 0 | NGHL | — |
| 22-GluCath | 47 | 195/26 | LC | 0 | 0 | NGHL | — |
| 15-BD-LC | 47 | 194/27 | LJS | 1 | 1 | NGHL | — |
| 16-BD-LC | 47 | 194/27 | LJI | 0 | 1 | NGHL | — |
| 17-BD-LC | 47 | 194/27 | LC | 1 | 1 | NGHL | — |
| 18-BD-LC | 47 | 195/26 | RJS | 1 | 1 | NGHL | — |
| 19-BD-LC | 47 | 195/26 | RC | 0 | 0 | NGHL | — |

Note that in the foregoing table "RC" means "Right Cephalic," "LJS" means "Left Jugular Vein Superior," "LJI" means "Left Jugular Vein Inferior," "RJS" means "Right Jugular Vein Superior," "RJI" means "Right Jugular Vein Inferior," and "NGHL" means "no gross or histologic legions." Furthermore, the numeric descriptions contained in the foregoing table with respect to the gross and microscopic fibrin buildup on the sensors is a shorthand for the following:

"0" indicates none, or limited to hemostatic plug at venipuncture site only;

"1" indicates scant discontinuous or microscopic deposition only;

"2" indicates <1 mm in thickness;

"3" indicates >1 mm in thickness; and

"4" indicates complete vascular occlusion (thrombosis).

These evaluations demonstrate that the GluCath sensor with heparin/benzalkonium coating was superior to the control catheters in terms of fewer instances of macroscopic fibrin deposits and fewer instances of microscopic fibrin deposition.

Example 5

Sustained Release Heparin

Figure 8:
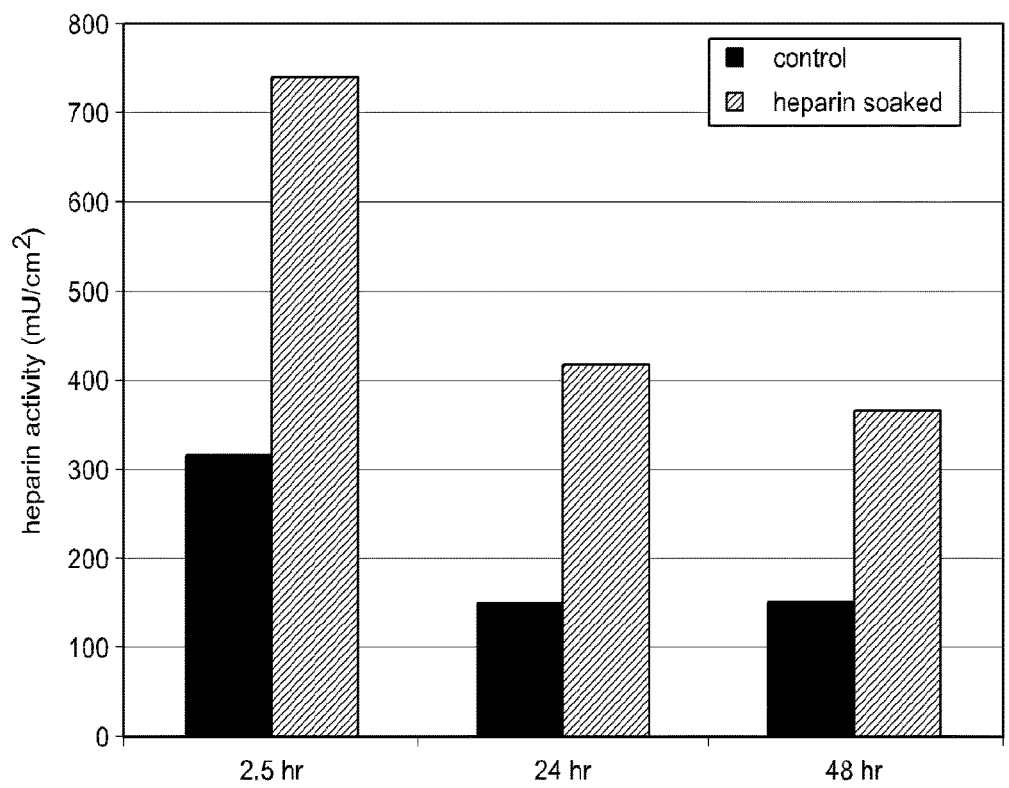
FIG. 8 shows the heparin activity of a glucose sensor that has undergone heparin soaking.

GluCath sensors were soaked in a 30% solution of sodium heparin in pH 5 phosphate buffered saline for two hours to saturate the hydrogel. After removal from the soak solution, the sensors were dip-coated with heparin benzalkonium in isopropyl alcohol to coat the outer surface. To serve as controls, other sensors which had not undergone the sodium heparin soaking step were also heparin benzalkonium dip-coated. After air drying overnight, the sensors were subjected to flowing buffer (pH 7.4 phosphate buffered saline at 37° C.) for up to 48 hours. At 2.5, 24, and 48 hours, the sensors were removed from the buffer and tested for heparin activity using a chromogenic anti-FXa activity assay. The results, shown in FIG. 8, showed that the heparin-soaked sensors retained higher levels of activity than the control sensors at each time point.

Example 6

Plasma Treatment and Covalent Attachment of Heparin

Heparin Attachment

Stock solutions of pH 5 2-(N-Morpholino)ethanesulfonic Acid (MES) (0.1M MES, 0.5M NaCl), Boc-amido-dPEG$_4$-acid (7 mL of 0.1 M), N-Hydroxysuccinimide (NHS) (7 mL of 0.2 M in pH 5 MES), sodium heparin (7 mL of 10 mg/mL in pH 5 MES), and ethylene dichloride (EDC) (7 mL of 0.2 M in pH 5 MES, made immediately before use) were prepared and stored at 4° C.

PES Membranes: To a 13×100 mm borosilicate culture tube was added 3 mL of Boc-amido-dPEG4-acid (4° C.), 3 mL of 0.2M NHS (4° C.), and 3 mL of 0.2M EDC (4° C.) and the solution was stored at 4° C. for 15 min. Eight PES membranes were glued to polyimide tubing and inserted into the solution through a septum and stored at 4° C. for 15 h. The excess reagent was removed and the membranes were washed with water (3×9 mL). In a separate tube, the membranes were treated with 0.275M HCl in 70% EtOH/H$_2$O for 3 h. The excess solution was removed and the membranes were washed with water (3×4 mL). In a separate culture tube 10 mg/mL sodium heparin (3 mL, 4° C.), 10 mM NHS (3 mL, 4° C.), and 10 mM EDC (3 mL, 4° C.) were added and the mixture was stored at 4° C. for 15 min. The PES membranes were inserted into the solution through a septum and the solution was stored at 4° C. for 15 h. The excess solution was removed and the membranes were air dried.

HDPE Membranes: To a 12×75 mm borosilicate culture tube was added 2 mL of Boc-amido-dPEG4-acid (4° C.), 2 mL of 0.2M NHS (4° C.), and 2 mL of 0.2M EDC (4° C.) and the solution was stored at 4° C. for 15 min. Five HDPE membranes were added to the solution and the mixture was stored at 4° C. for 15 h. The excess solution was removed and the membranes were washed with water (3×6 mL). In a separate tube, the membranes were treated with 0.275M HCl in 70% EtOH/H$_2$O for 3 h. The excess solution was removed and the membranes were washed with water (3×4 mL). In a separate culture tube 10 mg/mL sodium heparin (2 mL, 4° C.), 10 mM NHS (2 mL, 4° C.), and 10 mM EDC (2 mL, 4° C.) were added and the mixture was stored at 4° C. for 15 min. The HDPE membranes were transferred to the solution and the solution was stored at 4° C. for 15 h. The excess solution was removed and the membranes were air dried.

Production of Amino-Functionalized Membrane

Membranes were amino functionalized with nitrogen-containing plasmas by previously described methods. For example, Kull et al. (2005 *J Membrane Science* 246:203-215) describes surface modification with nitrogen-containing plasmas to produce hydrophilic membranes. Nitrogen and ammonia-based plasmas are used to modify a wide variety of polymer surfaces based on their ability to implant N-containing functionalities such as amine (—$NH_2$), imine (—CH=NH), amide (—$CONH_2$) and nitrile (C≡NH) groups. Referring to Favia, P. et al. (1996 *Plasmas and Polymers* 1(2): 91-112), plasma treatment may be done under conditions of radio frequency glow discharge plasma. For example, radio frequency glow discharges fed with $NH_3$ may be used to attach chemical groups onto polymers that are suitable for biomolecule immobilization.

Impact of Plasma on Membrane

Figure 9:
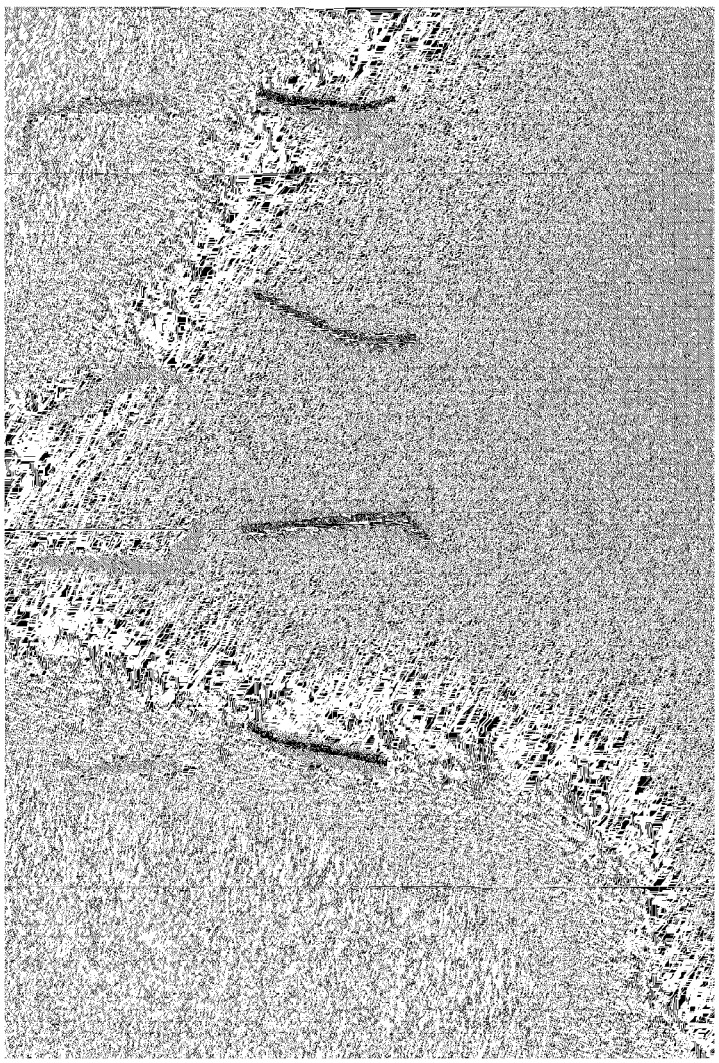
FIG. 9 shows the results of HDPE microporous membrane treated with $NH_3$ plasma and stained with a porphyrin stain or Bradford reagent.

Four different ammonia-plasma treatment conditions were evaluated (Experiment #s A, B, C, and D), wherein the extent of plasma treatment was varied. Condition D was the most aggressive treatment resulting in the greatest amount of amine functionalization on the surface of the membrane without damaging the integrity of the membrane. Proof of surface modification was established by staining with Porphyrin-$CO_2$H or Bradford reagent. As indicated in FIG. 9, the untreated mpms (controls) do not change color when dipped in staining solution, whereas the plasma treated samples become yellow or blue depending on the stain. The optimum conditions were chosen based on the intensity of the stain; condition D was selected for all future experiments.

Immobilization of Heparin

In order to covalently attach heparin to the amino-functionalized membrane two approaches were pursued: direct attachment and PEG-spacer attachment. Both approaches utilize EDC coupling in aqueous solution according to scheme 1. The amine groups react with the EDC/NHS activated carboxylic acids of PEG-acid or heparin and covalently bind the molecule to the surface.

Scheme 1. Reaction of heparin with amines on membrane surface to form amides.

Direct Attachment

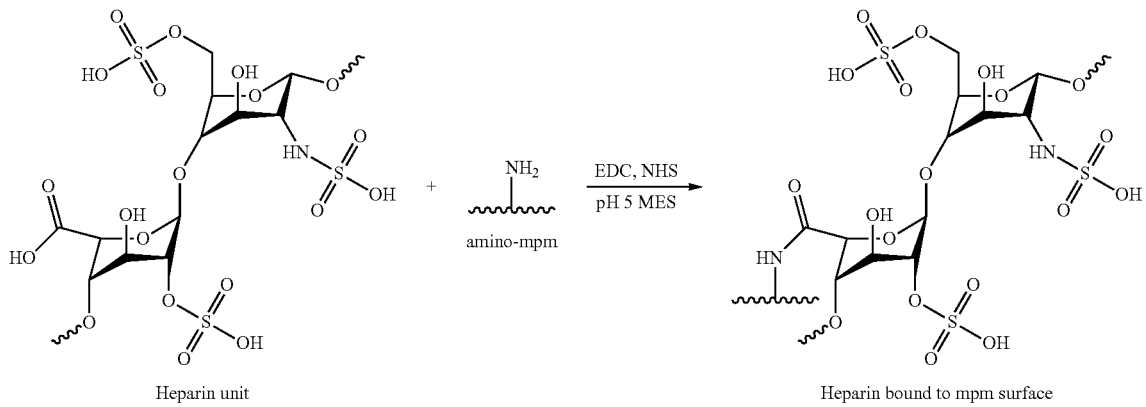

PEG-spacer Attachment

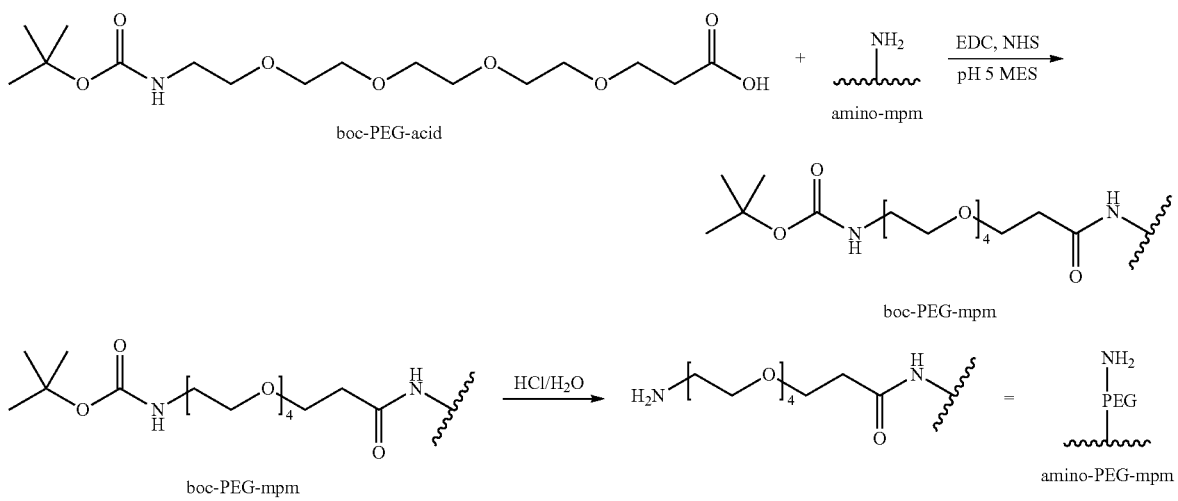

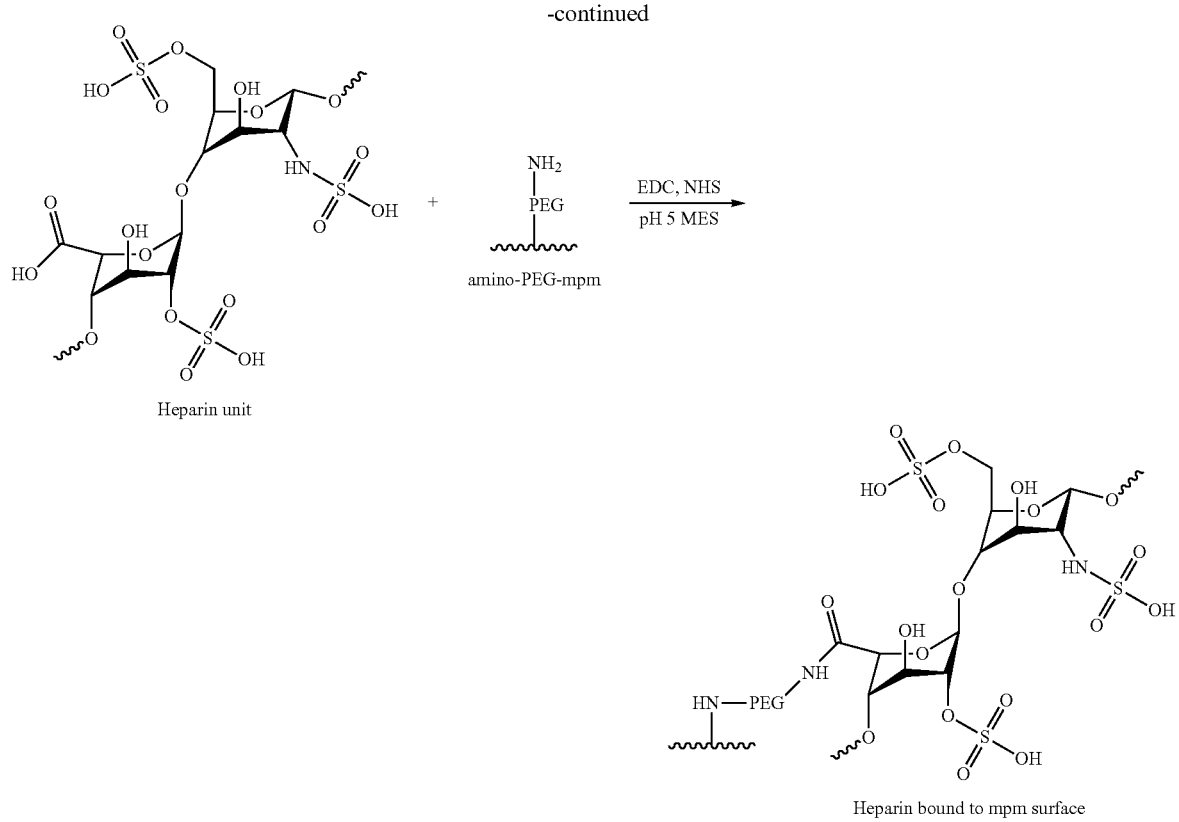

Heparin unit amino-PEG-mpm

Heparin bound to mpm surface

Various parameters were found to play an important role in the immobilization of heparin onto the surface of the membrane. These included pH, buffer composition, solvent, reaction temperature, reaction time, reaction vessel size, reaction vessel volume, deprotecting reagent type and concentration. All of these factors were evaluated during the development work. Additional factors that were also found to be important included EDC/NHS concentration, spacer, membrane type, and washing technique. In order to further optimize the heparin coating process four types of experiments were performed:

(1) Optimization of EDC/NHS concentration
(2) No spacer (Hep) vs. Spacer (PEG-Hep)
(3) HDPE vs. PES membrane
(4) Brine Wash vs. 24 h wash Each of the experiments was carried out with plasma treated membrane and the heparin activities were determined using a heparin assay. The data are summarized in the following tables.

TABLE 1

| Optimization of EDC/NHS concentration. | | |
|---|---|---|
| Exp # | [EDC]/[NHS] | Heparin Activity (mU/cm$^2$) |
| 1 | 200 mM | 119 ± 41% |
|   | 100 mM | 259 ± 49% |
|   | 10 mM | 965 ± 4% |
| 2 | 10 mM | 627 ± 58% |
|   | 1 mM | 404 ± 20% |
|   | 0.1 mM | 244 ± 9% |
|   | 0.01 mM | 530 ± 80% |

TABLE 1-continued

| Optimization of EDC/NHS concentration. | | |
|---|---|---|
| Exp # | [EDC]/[NHS] | Heparin Activity (mU/cm$^2$) |
| 3 | 20 mM | 1184 ± 82% |
|   | 10 mM | 2078 ± 92% |
|   | 5 mM | 802 ± 66% |

As indicated in Table 1, different concentrations of EDC/NHS gave different heparin activities. The heparin activity values are not necessarily comparable between experiments because of different assay conditions; however, there was a trend that indicated 10 mM to be the optimum concentration within each experiment and it was therefore selected as the optimum concentration.

The next study evaluated the use of PEG to form a spacer connecting heparin to the surface of the membrane. HDPE membranes were ammonia plasma treated and in one case heparin was directly coupled to the surface; in the second case a PEG spacer was attached then heparin was attached in a second step. As indicated in Table 2, the heparin activity was close to 200 times greater with the PEG spacer.

TABLE 2

| Spacer and no-spacer heparin activity. | | |
|---|---|---|
| Exp # | Heparin Activity (mU/cm$^2$) | Method |
| 4 | 14 ± 47% | HEP |
| 5 | 2078 ± 92% | PEG-HEP |

The data in Tables 1 and 2 can be explained based on the current knowledge of immobilized heparin (Ratner B. D.;

Hoffman, A. S.; Schoen, F. J.; Lemons J. E. *Biomaterials Science, An Introduction to Materials in Medicine, 2$^{nd}$ Edition.*). In general, higher heparin activity is obtained when heparin is bound to the surface through single point attachment. Adding less of the coupling agents probably results in less modification to the heparin molecule and activates fewer of its carboxylic acids towards nucleophilic attack by the amino surface. However, going too low in concentration results in little heparin actually being bound to the surface. The optimum procedure allows for effective attachment of heparin to the surface with minimal chemical modification to the heparin active sites.

The PEG-spacer is thought to allow for more degrees of freedom for heparin. The PEG lines up on the surface in a vertical arrangement and leaves room for heparin to move about with less restriction than if it was bound directly to the surface. This is believed to improve the heparin activity.

Figure 10:
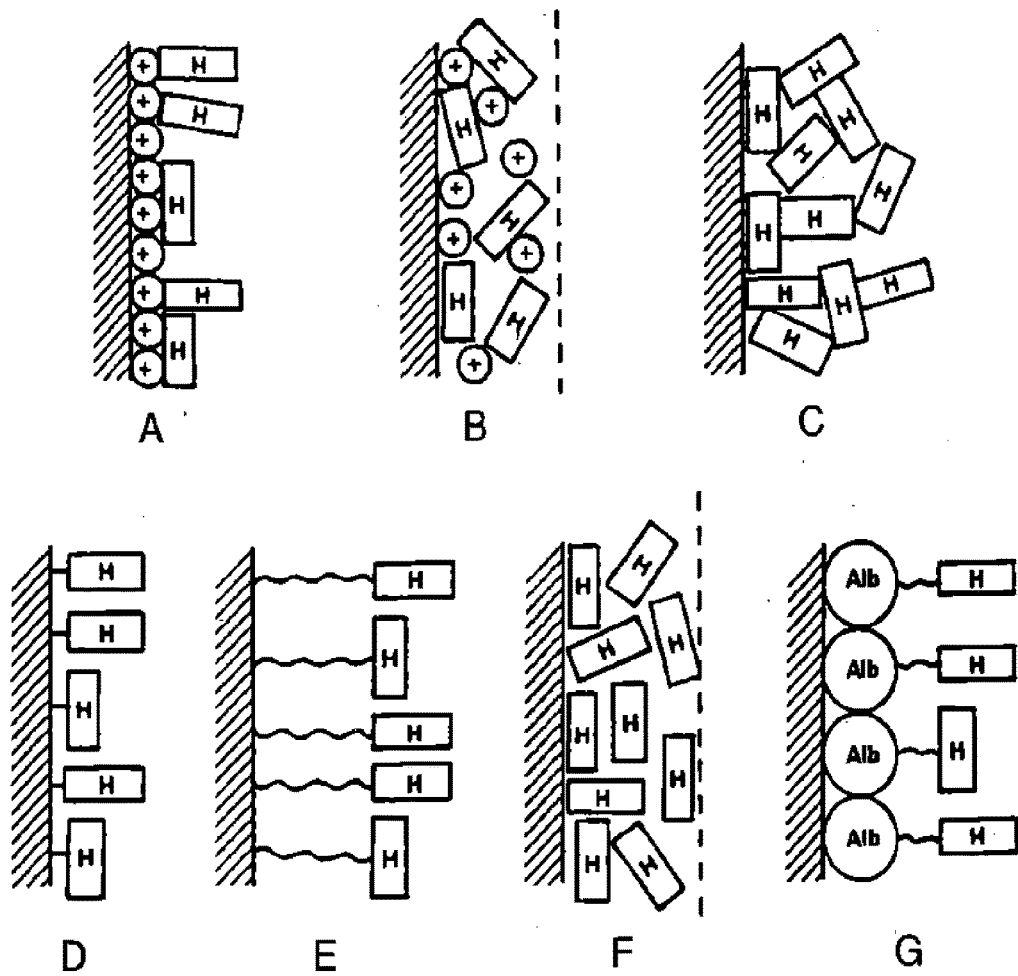
FIG. 10 shows various arrangements of heparin on the surface of a biomaterial.

To better illustrate these concepts, examples of heparin bound to the surface of a biomaterial are given in FIG. 10. Panel A depicts Hep ionically bound to the surface, B describes Hep ionically bound to a counterion, C represents the current HBAC (Surmodics) method where Hep physically coats the surface, D and E represent single point attachment of heparin with and without a spacer, F illustrates Hep dispersed in a hydrophobic polymer, and G illustrates Hep immobilized as a conjugate with albumin.

When heparin is attached at a single point (as in D, E, and G), it has more degrees of freedom and retains its activity and ability to bind antithrombin. In some cases, heparin is attached from a single site in the heparin to a single site on an amino-functionalized membrane or to a spacer. As it relates to our system, direct attachment of heparin (D) and PEG-spaced attachment (E) can be considered attempts at single point attachment. In these cases, heparin is attached from a single site in the heparin molecule to a single site on an amino-functionalized membrane or to a spacer. True single point attachment is obtained by chemically modifying heparin with periodate, which is the approach that Carmeda AB (Upplands Vasby, Sweden) uses. The strategy disclosed herein is novel and simpler.

The final experiment was to compare the activities of 3 different membranes after coating them with the in-house coating. To do this PES1, PES2 and HDPE membranes were coated with PEG-heparin and tested after a brine wash and a 24 h PBS wash. Table 3 summarizes this data.

TABLE 3

Comparison of different membranes with in-house coating after washes.

| | | Heparin Activity | |
|---|---|---|---|
| Exp # | Membrane (sample size) | Brine Wash | 24-Hour Wash |
| 6 | PES1(n = 6) | 1117 ± 43% | 84 ± 10% |
| 7 | HDPE (n = 6) | 1715 ± 44% | 14 ± 22% |
| 8 | PES2 (Post PBS wash, n = 11) | 2550 ± 39% | 130 ± 52% |

As indicated in Table 3, both PES membranes have a higher long term activity (24 h wash) then HDPE. In addition, PES2 has higher initial activity (after brine wash). This demonstrates that PES is a better substrate for covalent attachment of heparin.

All references cited herein, including but not limited to published and unpublished applications, patents, and literature references, and also including but not limited to the references listed in the Appendix, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A method of covalently attaching heparin to an analyte-permeable membrane on an analyte sensor comprising:
   providing an analyte sensor, the analyte sensor including
      an optical fiber defining a light path;
      an analyte-responsive chemical indicator system comprising a fluorophore operably coupled to an analyte binding moiety, wherein the chemical indicator system is disposed within the light path along a distal portion of the optical fiber and wherein said indicator system is capable of generating a signal related to a concentration of analyte, and wherein the fluorophore generates a fluorescence emission signal when excited by light and a glucose binding moiety to modulate the florescence emission signal; and
      an analyte-permeable membrane covering the indicator system at least along the distal portion of the optical fiber;
   plasma treating the analyte-permeable membrane to produce an amino-functionalized membrane; and
   reacting the amino-functionalized membrane with heparin under conditions in which heparin becomes covalently attached to the amino-functionalized membrane, wherein said heparin is indirectly attached via a spacer to said amino-functionalized membrane and/or said heparin is attached from a single site in said heparin to a single site on said amino-functionalized membrane or to said spacer.

2. The method of claim 1, wherein said plasma treatment is conducted with radio frequency glow discharge plasma.

3. The method of claim 1, wherein said plasma is selected from the group consisting of, allylamine and NH$_3$.

4. The method of claim 1, comprising the following step:
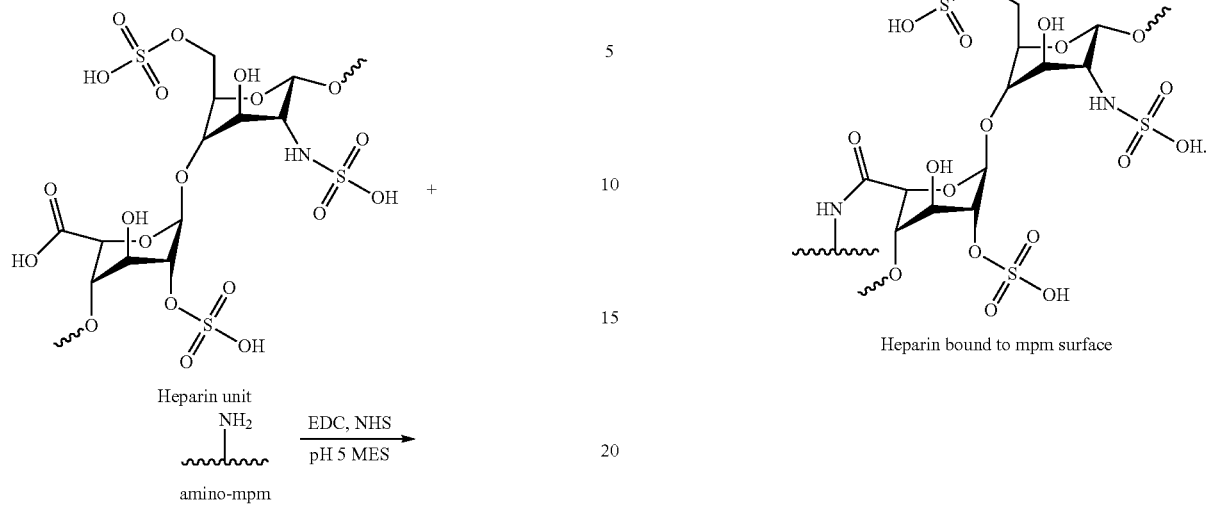
5. The method of claim 1 comprising the following steps:
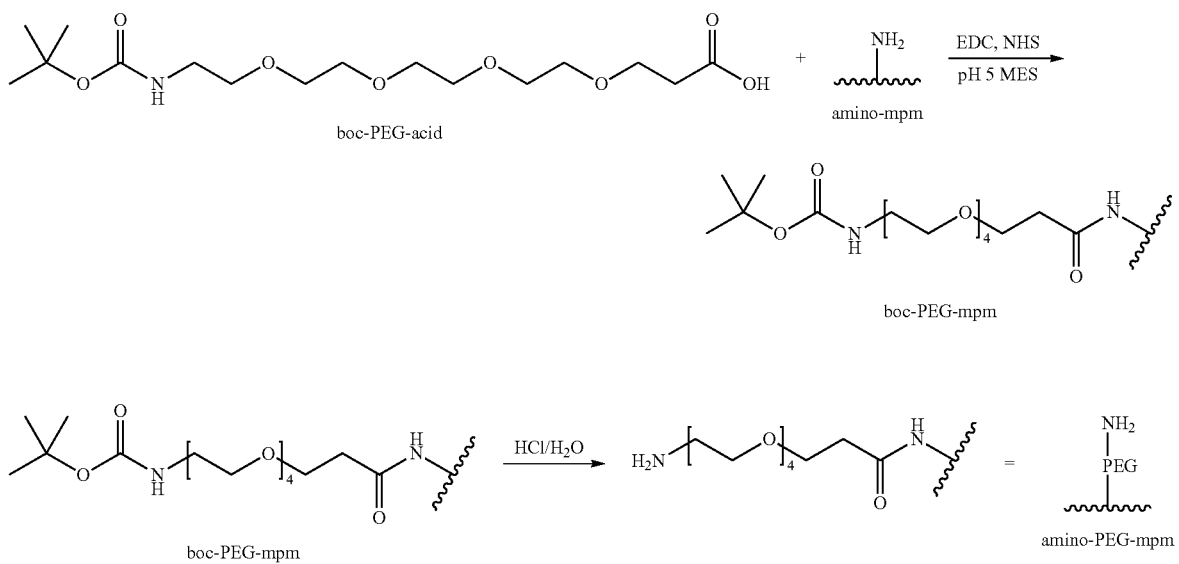
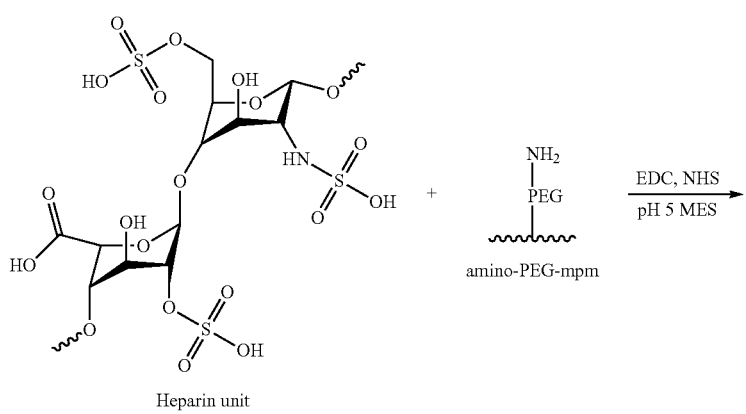

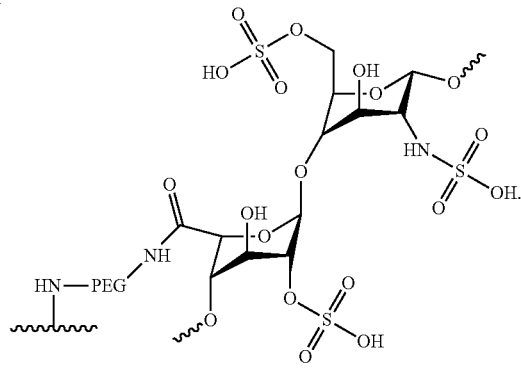

Heparin bound to mpm surface

6. The method of claim 4 or 5, wherein said EDC/NHS concentration is 10 mM.

7. The method of claim 1, wherein said analyte-permeable membrane is PES membrane.

8. The method of claim 1, wherein said analyte-permeable membrane is associated with a hollow fiber that encloses an analyte-responsive indicator.

9. An analyte sensor comprising:
an optical fiber defining a light path;
an analyte-responsive chemical indicator system comprising a fluorophore operably coupled to an analyte binding moiety, wherein the chemical indicator system is disposed within the light path along a distal portion of the optical fiber, and wherein said indicator system is capable of generating a signal related to a concentration of analyte, and wherein the fluorophore generates a fluorescence emission signal when excited by light and a glucose binding moiety to modulate the florescence emission signal; and
an analyte-permeable membrane covering the indicator system at least along the distal portion of the optical fiber;
a coating comprising heparin covalently bound to at least a portion of the analyte-permeable membrane,
wherein said heparin is indirectly attached via a spacer to said analyte-permeable membrane and/or said heparin is attached from a single site in said heparin to a single site on said analyte-permeable membrane or to said spacer.

10. The sensor of claim 9, wherein said analyte-permeable membrane is a porous membrane.

11. The sensor of claim 9, wherein said analyte-permeable membrane is associated with a hollow fiber that encloses the analyte responsive indicator.

12. The sensor of claim 9, wherein a cross-sectional geometry of at least a portion of the sensor is placed in a blood vessel lumen.

13. The method of claim 1, wherein said spacer is polyethylene glycol and wherein said membrane is selected from the group consisting of polyethersulfone (PES) membrane, polyethersulfone/polyvinylpyrrolidone (PES/PVP) blend membrane and High Density Polyethylene (HDPE) membrane.

14. The method of claim 1, wherein the fluorophore is HPTS-triCysMA.

15. The method of claim 1, further including contacting the analyte-permeablfe membrane with a solution of benzalkonium and heparin.

16. The method of claim 1, wherein the reacting the amino-functionalized membrane with heparin includes soaking the amino-functionalized membrane in an aqueous heparin solution for at least one hour.

17. The sensor of claim 9, wherein the fluorophore is HPTS-triCysMA.

18. The sensor of claim 9, wherein the fluorophore and the analyte binding moiety are immobilized within a water-insoluble organic polymer.

19. The sensor of claim 18, wherein the analyte binding moiety is 3,3'-oBBV and the water-insoluble organic polymer is a DMAA (N,N-dimethylacrylamide) hydrogel matrix.

* * * * *